US010455936B2

(12) United States Patent
McKnight et al.

(10) Patent No.: US 10,455,936 B2
(45) Date of Patent: Oct. 29, 2019

(54) METHOD AND APPARATUS FOR DISPENSING SANITIZER FLUID, OPENING DOORS, AND RECORDING DATA PERTAINING TO HAND SANITIZATION

(71) Applicant: Altitude Medical, Inc., Chardon, OH (US)

(72) Inventors: Jacob Vincent McKnight, Long Hanborough (GB); Richard James Gilbert, London (GB); Adam Wilmore Paterson, West Linton (GB); Matthew David Laws, London (GB); Nicholas Hooton, London (GB); Gregg Alan Henderson, Munroe Falls, OH (US)

(73) Assignee: Altitude Medical, Inc., Chardon, OH (US)

( * ) Notice: Subject to any disclaimer, the term of this patent is extended or adjusted under 35 U.S.C. 154(b) by 0 days.

(21) Appl. No.: 15/588,518

(22) Filed: May 5, 2017

(65) Prior Publication Data
US 2017/0318964 A1 Nov. 9, 2017

Related U.S. Application Data

(60) Provisional application No. 62/333,109, filed on May 6, 2016.

(51) Int. Cl.
*A47B 95/02* (2006.01)
*A61L 2/18* (2006.01)
(Continued)

(52) U.S. Cl.
CPC ............ *A47B 95/02* (2013.01); *A47K 5/1202* (2013.01); *A61L 2/0088* (2013.01); *A61L 2/18* (2013.01);
(Continued)

(58) Field of Classification Search
CPC .... A47B 95/02; A47K 5/1202; A47K 5/1217; A61L 2/0088; A61L 2/18; A61L 2/22;
(Continued)

(56) References Cited

U.S. PATENT DOCUMENTS 2,044,904 A 6/1936 Heisig
D201,063 S 5/1965 Julius
(Continued)

FOREIGN PATENT DOCUMENTS

CA 2296152 A1 6/2000
CH 568074 A5 10/1975
(Continued)

OTHER PUBLICATIONS

Australian Office Action dated Jul. 3, 2012 for Australian Patent Application No. 2008262456 (3 pages).
(Continued)

*Primary Examiner* — Patrick M. Buechner
(74) *Attorney, Agent, or Firm* — Schwegman Lundberg & Woessner, P.A.

(57) ABSTRACT

Devices, systems, and methods for promoting hand sanitization which may be mounted above or near a door handle. Hand sanitization devices include a sanitizer agent cartridge disposed inside a housing body and fluidically coupled to an actuating pump. The pump is configured to dispense the sanitizer when an actuation mechanism is pushed or pulled. The cartridge is also coupled to a pump sheath disposed below the pump so as to protect the internal components of the devices from unintentional splashing by the sanitizer agent. The hand sanitization devices may also record when the door is opened, when the sanitizer is dispensed, if the cartridge is empty, and when a user is approaching the door.

(Continued)

The hand sanitization devices also have a user interface system configured to encourage the approaching user to sanitize their hands.

9 Claims, 20 Drawing Sheets

(51) Int. Cl.

| | | |
|---|---|---|
| *E05B 1/00* | (2006.01) | |
| *A61L 2/22* | (2006.01) | |
| *A47K 5/12* | (2006.01) | |
| *A61L 2/00* | (2006.01) | |
| *B05B 11/00* | (2006.01) | |
| *G08B 21/24* | (2006.01) | |

(52) U.S. Cl.
CPC ............ *A61L 2/22* (2013.01); *B05B 11/3052* (2013.01); *B05B 11/3057* (2013.01); *E05B 1/0069* (2013.01); *G08B 21/245* (2013.01); *A61L 2202/14* (2013.01)

(58) Field of Classification Search
CPC ............ A61L 2202/14; A61L 2202/12; A61L 2202/15; A61L 2202/20; B05B 11/3052; B05B 11/3057; E05B 1/0069; G08B 21/245
See application file for complete search history.

(56) References Cited

U.S. PATENT DOCUMENTS

| | | | |
|---|---|---|---|
| 3,967,478 A | 7/1976 | Guinn | |
| 4,046,508 A | 9/1977 | McDonald | |
| 4,402,432 A | 9/1983 | Corsette | |
| 4,710,634 A | 12/1987 | Brookes | |
| 4,896,144 A | 1/1990 | Bogstad | |
| 4,997,139 A | 3/1991 | Menard | |
| 5,017,035 A | 5/1991 | Peters et al. | |
| 5,454,409 A | 10/1995 | McAffer et al. | |
| 5,688,251 A | 11/1997 | Chanoch | |
| 5,695,091 A | 12/1997 | Winings et al. | |
| D397,434 S | 8/1998 | Pike | |
| 5,808,553 A | 9/1998 | Cunningham | |
| 5,945,910 A * | 8/1999 | Gorra ................... | G08B 21/245 340/573.1 |
| 6,029,557 A | 2/2000 | Sulm et al. | |
| 6,029,600 A | 2/2000 | Davis | |
| 6,031,461 A | 2/2000 | Lynn | |
| 6,147,607 A | 11/2000 | Lynn | |
| 6,211,788 B1 | 4/2001 | Lynn et al. | |
| 6,289,557 B1 | 9/2001 | Manson et al. | |
| 6,425,885 B1 | 7/2002 | Fischer et al. | |
| 6,577,240 B2 | 6/2003 | Armstrong | |
| 6,645,435 B2 | 11/2003 | Dawson et al. | |
| 6,874,697 B2 | 4/2005 | Callueng | |
| 6,997,394 B1 | 2/2006 | Washington | |
| 7,080,427 B1 | 7/2006 | Campopiano et al. | |
| D543,624 S | 5/2007 | Khalaj | |
| 7,242,307 B1 * | 7/2007 | LeBlond .............. | G08B 21/245 340/573.1 |
| 7,320,418 B2 | 1/2008 | Sassoon | |
| 7,338,646 B2 | 3/2008 | Gilbert | |
| 7,458,742 B2 | 12/2008 | Stropkay et al. | |
| 7,563,253 B2 | 7/2009 | Tanner et al. | |
| 8,282,297 B2 | 10/2012 | Ryan et al. | |
| 8,299,896 B2 | 10/2012 | Mahmoodi et al. | |
| 8,353,085 B2 | 1/2013 | Balzano | |
| 8,408,423 B1 | 4/2013 | McKnight et al. | |
| D709,196 S | 7/2014 | Greep et al. | |
| D719,255 S | 12/2014 | Ohashi | |
| D729,382 S | 5/2015 | Kunze | |
| D740,410 S | 10/2015 | Korkuch et al. | |
| 9,192,514 B2 | 11/2015 | Mita et al. | |
| D744,644 S | 12/2015 | Lee et al. | |
| 9,649,398 B1 * | 5/2017 | York ........................ | A61L 2/24 |
| 2002/0041824 A1 | 4/2002 | Dawson et al. | |
| 2002/0127139 A1 | 9/2002 | Lidahl et al. | |
| 2004/0026530 A1 | 2/2004 | Callueng | |
| 2004/0223894 A1 | 11/2004 | Gilbert | |
| 2004/0237255 A1 | 12/2004 | Lin et al. | |
| 2005/0173459 A1 | 8/2005 | Buxmann | |
| 2006/0038417 A1 | 2/2006 | Pudney | |
| 2006/0153733 A1 | 7/2006 | Sassoon | |
| 2006/0243762 A1 * | 11/2006 | Sassoon ................ | A61L 2/18 222/649 |
| 2006/0245818 A1 | 11/2006 | Stropkay et al. | |
| 2007/0207073 A1 | 9/2007 | Drucker | |
| 2007/0229288 A1 | 10/2007 | Ogrin et al. | |
| 2008/0023505 A1 | 1/2008 | Sassoon | |
| 2008/0131332 A1 * | 6/2008 | Nguyen .................. | A61L 2/24 422/119 |
| 2008/0305020 A1 | 12/2008 | Oshmyansky | |
| 2009/0195385 A1 * | 8/2009 | Huang ................ | G08B 21/245 340/572.1 |
| 2009/0219131 A1 * | 9/2009 | Barnett ................ | G08B 21/245 340/5.2 |
| 2009/0224924 A1 * | 9/2009 | Thorp ................. | G08B 21/245 340/573.1 |
| 2009/0265990 A1 * | 10/2009 | Stratmann ................ | A47K 5/12 49/31 |
| 2009/0295539 A1 | 12/2009 | Mahmoodi et al. | |
| 2010/0140499 A1 * | 6/2010 | Casale .................. | E05B 1/0069 250/454.11 |
| 2010/0252568 A1 * | 10/2010 | Ciavarella ............ | A47K 5/1202 222/1 |
| 2010/0294806 A1 | 11/2010 | McDowell | |
| 2010/0327000 A1 * | 12/2010 | Winslow ................ | A47K 10/46 221/1 |
| 2011/0011886 A1 | 1/2011 | Zaima et al. | |
| 2011/0025509 A1 * | 2/2011 | Brow ...................... | A47K 5/06 340/573.1 |
| 2011/0174992 A1 | 7/2011 | Sakita | |
| 2012/0080451 A1 | 4/2012 | Williams et al. | |
| 2012/0112914 A1 * | 5/2012 | Wegelin .............. | A47K 5/1217 340/573.1 |
| 2012/0144610 A1 | 6/2012 | Balzano | |
| 2012/0218106 A1 | 8/2012 | Zaima et al. | |
| 2012/0251387 A1 * | 10/2012 | Samaras ................ | E05B 1/0069 422/28 |
| 2012/0305804 A1 | 12/2012 | Goldman | |
| 2013/0145692 A1 * | 6/2013 | Laird ...................... | E05F 15/73 49/31 |
| 2014/0253336 A1 | 9/2014 | Ophardt et al. | |
| 2014/0266730 A1 * | 9/2014 | Hines ................... | G08B 21/245 340/573.1 |
| 2015/0308149 A1 | 10/2015 | Oshmyansky et al. | |
| 2015/0328349 A1 * | 11/2015 | Robert .................. | A61L 2/0094 422/22 |
| 2016/0067363 A1 | 3/2016 | Robert | |
| 2016/0179089 A1 * | 6/2016 | Stratmann ............. | E05B 1/0069 700/231 |
| 2016/0230418 A1 * | 8/2016 | Allred .................. | B05B 11/3052 |
| 2017/0165387 A1 * | 6/2017 | Robert ...................... | A61L 2/14 |
| 2017/0246332 A1 * | 8/2017 | Marshall ................... | A61L 2/08 |
| 2018/0344887 A1 * | 12/2018 | Chen ........................ | A61L 2/24 |

FOREIGN PATENT DOCUMENTS

| | | |
|---|---|---|
| DE | 19857268 A1 | 6/2000 |
| DE | 10014472 A1 | 10/2001 |
| DE | 202004006845 U1 | 8/2004 |
| EP | 2428627 A1 | 3/2012 |
| FR | 2780744 A1 | 1/2000 |
| GB | 2402622 A | 12/2004 |
| GB | 2421897 A | 7/2006 |
| GB | 2436284 A | 9/2007 |
| GB | 2484650 A | 4/2012 |
| GB | 2510041 A | 7/2014 |
| JP | H07327763 A | 12/1995 |
| WO | WO-0035496 A1 | 6/2000 |

(56) References Cited

FOREIGN PATENT DOCUMENTS

| WO | WO-2007107784 A2 | 9/2007 |
| WO | WO-2016046333 A1 | 3/2016 |
| WO | WO-2017193088 A1 | 11/2017 |
| WO | WO-2017193088 A8 | 12/2017 |

OTHER PUBLICATIONS

European Office Action dated Nov. 2, 2012 for European Application No. 11192484.1 (4 pages).
European Search Report dated Mar. 1, 2016 for European Application No. 13833003.0 (6 pages).
Extended European Search Report dated Jan. 11, 2012 for European Application No. 11192484.1-2113.
International Preliminary Report on Patentability dated Dec. 17, 2009 for Application PCT/US2008/006505.
International Search Report and Written Opinion dated Sep. 25, 2017 for International Application No. PCT/US2017/031429.
International Search Report and Written Opinion dated Nov. 7, 2013 for PCT Application No. PCT/US2013/053586.
International Search Report and Written Opinion dated Nov. 12, 2008 for PCT Application No. PCT/US2008/006505.
Supplementary European Search Report dated Jun. 6, 2011 for Application No. 08754618.0-2113/2155266 (PCT/US2008006505).
"International Application Serial No. PCT/US2017/031429, International Preliminary Report on Patentability dated Nov. 15, 2018", 11 pages.
"International Application Serial No. PCT/US2017/031429, Invitation to Pay Additional Fees dated Jul. 14, 2017", 3 pages.

\* cited by examiner

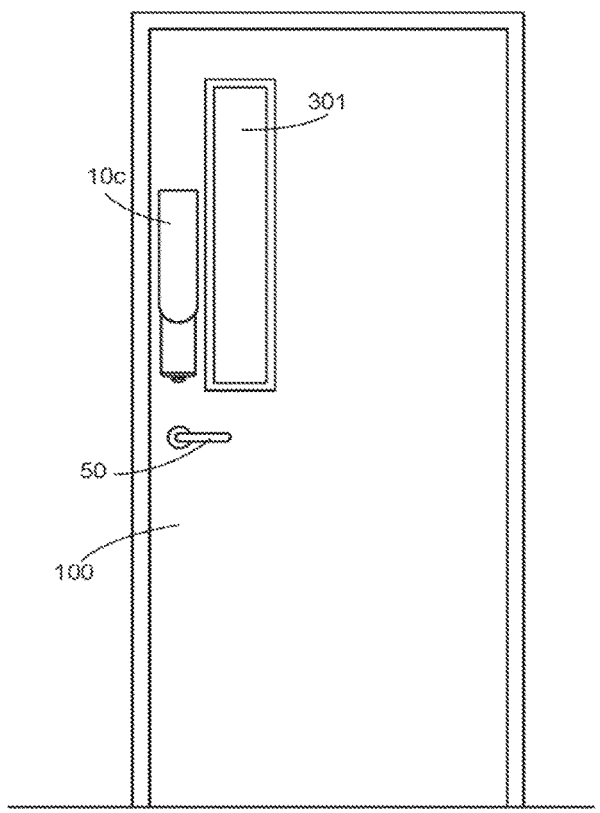
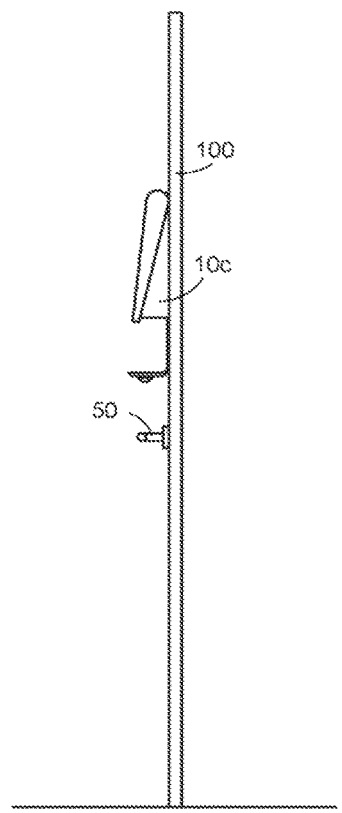
FIG. 3A  FIG. 3B
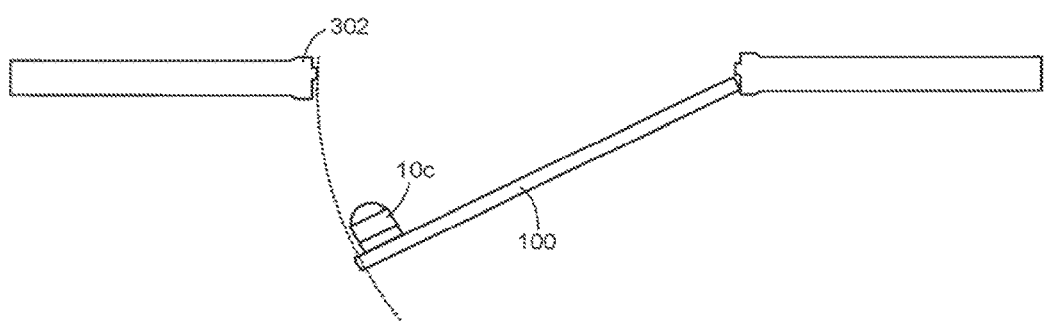
FIG. 3C

METHOD AND APPARATUS FOR DISPENSING SANITIZER FLUID, OPENING DOORS, AND RECORDING DATA PERTAINING TO HAND SANITIZATION

CROSS-REFERENCE

This application claims the benefit of U.S. Provisional Application No. 62/333,109, filed 6 May 2016, the entire content of which is incorporated herein by reference.

This application is related to the following patent application: PCT application Serial No. PCT/US2013/053586, the entire content of which is incorporated herein by reference.

BACKGROUND OF THE INVENTION

Field of the Invention

The present application generally relates to health care technology and, in particular, to methods, systems, and apparatus for promoting hand sanitization preferably via door-mounted sanitizer dispensers.

Background

Prevention of the spread of disease is a major concern in the workplace. In many cases, germs are transferred from one person to another through shared contact with workplace surfaces. In particular, door handles may be especially susceptible to acquiring and passing on infectious organisms. Hand sanitization may be effective in reducing an individual's risk of acquiring an infection from contact with non-sterile door handles. For example, the link between hand sanitization and hospital-acquired infections, such as Methicillin-resistant *Staphylococcus aureus* (MRSA) and *C. difficile*, is well-established. Many workplaces which require good hand hygiene, for example hospitals or other medical facilities, places where food manufacturing or processing occurs, restaurants, cruise ships, public bathrooms, and military facilities, have installed sanitizer dispensers in an effort to combat the spread of infections. Despite this, the rates of hand cleanliness in such workplaces have not risen substantially or as dramatically as would be necessary to significantly reduce infections.

In many instances, the placement of current hand sanitizer dispensers is such that they do not promote usage, for example on a wall away from the source of contamination to the hands (e.g. a door handle). It is therefore desirable to provide a hand sanitization device which may be placed in the path of the user, for example on a door, in order to give users easier access to the device and thereby promote use. In order to address this positioning problem, many inventors have attempted to modify the door handle to enable it to deliver sanitizer to the hand of a user as they operate the door. By creating a handle dispenser, it was thought that hand sanitization rates would improve as the user was required to sanitize their hands in order to pass through the door. It would therefore be desirable to provide a hand sanitization device which may be placed in the path of the user.

Furthermore, automatic dispensing of the sanitizer fluid from the handle can lead to spilling of the fluid onto the floor if the user is not ready (for example if the hand is not properly positioned on the handle to receive the sanitizer) or if something other than a hand is used to operate the handle (for example an elbow if the hands are full). For example, when a user grips a normal "twisting" lever handle, the hand is positioned such that the palm of the hand is facing downward and in contact with the handle. This "natural" hand position does not allow the user to "catch" the sanitizer with the hand and thus may lead to increased spillage. Some handle dispensers have tried to address this problem by designing a handle so as to prescribe an unnatural grip which would allow the hand sanitizer to be dispensed into and caught by the palm of the hand. However, such designs force the user to put their hand in an unnatural position that suits sanitization and thus unduly burdens the user, contrary to the goal of the handle dispenser to make hand sanitization easier. Some handle dispensers have been designed to address the problem of hand positioning, for example by spraying the sanitizer upwards into the palm of the user as in U.S. Pat. No. 8,505,782 or by dropping sanitizer onto the back of the hand as it grips the handle as in U.S. patent application Ser. No. 12/930,607, the entire contents of which are incorporated herein by reference. In both cases, the hand is more naturally positioned and the handle maintains a standard configuration. In some circumstances however spillage may occur. It would therefore be desirable to provide a hand sanitization device which may be placed in the path of the user, configured to prevent spillage, and which allows the user to grip the handle naturally.

Handle dispensers are further limited in their utility in that there are many different types, sizes, and styles of doors which may comprise or require a similarly broad range of handles. Many types of handles may be specified by architects or building managers in order to meet a variety of needs in a building. For example, anti-ligature handles may be desired in places with vulnerable people. Wide grip handles may be useful for people with disabilities. Paddle-style handles may be used to operate latches. Simple "door pulls" may be desired in workplaces where a locking mechanism is not needed, thus the door pull functions only to provide a grip. The doors may be a wide variety of thicknesses and may be fitted with multiple types of proprietary locks or latches which serve different purposes for different workplace needs. Designing and manufacturing handle dispensers to match or replace the various handle/door combinations possible would be very inefficient and could be quite costly. It would therefore be desirable to provide a hand sanitization device which may be deployed on existing doors in a workplace setting without requiring re-design and manufacture of the device or reconfiguration of the doors in order to utilize it.

Current wall-mounted hand sanitizer dispensers could potentially be fitted on doors so as to avoid the problems inherent with a handle dispenser design, but they would suffer a wide variety of problems in at least some instances. Standard sanitizer dispensers are often bulky or awkward to mount on a door. For example, some doors have windows positioned near the edge of the door which allow the user to see to the opposite side of the door as they approach so as to avoid a collision. Current dispensers are often sized such that they are restricted by their width in the placement of the dispenser to the side of the window away from the free edge of the door and out of the line of sight of the user. Additionally, many current dispensers are sized such that they are restricted by their depth to placement on a door, even one without a window, out of the direct line of site of user in order to prevent the dispenser from hitting the door frame or another door (for example in case of a double door). Furthermore, such placement may require the user to reach across themselves to operate the dispenser or to open the door, further restricting the utility of the device for preventing the spread of infections. Some dispensers have been designed with slim profiles in order to be used in more confined spaces, however many of them have traded sanitizer volume for a space-saving housing and can hold only a small volume of sanitizer fluid, thus these dispensers require regular refilling. It would therefore be desirable to provide a hand sanitization device which may be placed in the path of the user and which is sized and shaped to allow for placement of the device within the line of site of the user to encourage hand sanitization while still being large enough to hold a standard amount of sanitizer fluid.

Furthermore, current wall-mounted hand sanitizer dispensers are commonly made from plastics and are cheaply made such that they lack durability and long-term use potential. It would therefore be desirable to provide a hand sanitization device which may be placed in the path of the user and which is durable enough to withstand frequent use over long periods of time.

While many wall-mounted hand sanitizer dispensers comprise electronic systems aimed at measuring the rate of hand sanitization, they are limited in the type of data they can measure. A typical wall-mounted sanitizer dispenser can only generate data relative to time, for example the number or percentage of sanitization events in an hour. They cannot be used to determine how many users have passed by the dispenser and opted out of sanitizing their hands, a much more useful metric of dispenser use when analyzing hand hygiene behavior in a population in order to develop tools to encourage sanitization use, without being paired with external, discrete sensors. It would therefore be desirable to provide a hand sanitization device which may be placed in the path of the user and which can measure the rate of hand sanitization in reference to time as well as user opportunity.

At least some of these challenges are addressed by the disclosure provided herein.

SUMMARY OF THE INVENTION

The present invention generally relates to health care technology and, in particular, to methods, systems, and apparatus for promoting hand sanitization via door-mounted sanitizer dispensers.

In a first aspect, a hand sanitization device is provided. The hand sanitization device comprises a housing configured to be mounted on a door, the door comprising a handle. A cartridge containing sanitizer agent and an actuatable pump are disposed within the housing. The cartridge is operably coupled to the actuatable pump such that actuation of the actuatable pump causes the cartridge to dispense the sanitizer agent to a user's hand. An actuation mechanism is operably coupled to the actuatable pump and movable from a first position to a second position. Movement of the actuation mechanism from the first position to the second position actuates the pump. The device also comprises a pump sheath adjacent the pump and coupled to the cartridge. The pump sheath acts to protect internal components in the housing from being splashed by the sanitizer agent when dispensed from the pump.

Optionally, the actuation mechanism may be configured to be moved from the first position to the second position by the user's hand.

Optionally, the hand sanitization device may further comprise a sensor. The actuation mechanism may be configured to be moved from the first position to the second position automatically in response to detection of the user's hand by the sensor.

Optionally, the hand sanitization device may further comprise a user interface system the user interface system comprising an indicator element. The user interface system may be configured to encourage the user to sanitize their hands. The indicator element may comprise one or more of a display, an audio indicator or cue, a tactile or touch indicator, a smell indicator, a colored light, or a plurality of colored lights.

Optionally, the hand sanitization device may further comprise an accelerometer configured to detect movement of the door. The accelerometer may be configured to detect a door opening event when movement of the door is detected. The accelerometer may be configured to activate one or more of a user interface system or a door sensor when movement of the door is detected.

Optionally, the hand sanitization device may further comprise a proximity sensor configured to sense the user approaching the door. The proximity sensor may be configured to activate one or more of a user interface system or a door sensor when an approaching user is sensed.

Optionally, the hand sanitization device may further comprise a display coupled to the housing. The display may be configured to project one or more images designed to encourage the user to use the hand sanitization device.

Optionally, the hand sanitization device may further comprise a sanitization event sensor configured to detect a sanitization event when the actuation mechanism has moved from the first position to the second position. The sanitization event sensor may for example comprise a mechanical switch or a magnetic switch.

Optionally, the device may further comprise a drip sensor configured to detect a drip event when the sanitizer agent is dispensed. The drip sensor may comprise an infra-red sensor. The pump sheath may be formed from an optically transparent material through which infra-red radiation transmits.

Optionally, the hand sanitization device may further comprise a door sensor configured to detect a door opening event when a presence of a user's second hand on the handle is detected. The door sensor may comprise an infra-red sensor configured to emit a beam of infra-red radiation to a pre-determined point. The pre-determined point may be one or more of above, behind, or in front of the handle.

Optionally, the device may further comprise a control circuit configured to collect data, collate data, or transmit data. The data may comprise one or more of a drip event, a door opening event, a sanitization event, or a ratio of sanitization events to door opening events for a pre-determined number of users.

Optionally, the hand sanitization device may further comprise a drip tray positioned below the actuatable pump. The drip tray may be configured to capture the sanitizer agent which does not reach the user's hand.

Optionally, the actuation mechanism may comprise one or more of a moveable panel, a moveable arm, a lever, a switch, a button, a wedge, a knob, a pull, a solenoid, or a sensor in combination with a solenoid.

Optionally, the sanitizer agent may comprise one or more of an alcohol fluid, an alcohol gel, an alcohol foam, a fungicidal agent, a virucidal agent, or a biocidal agent.

Optionally, the cartridge may be configured to hold a volume of sanitizer agent within a range of about 600 ml to about 800 ml.

Optionally, the actuation mechanism may comprise a biasing element configured to move the actuation mechanism from the second position to the first position after the sanitizer agent has been dispensed from the actuatable pump.

Optionally, the actuatable pump may comprise one or more of a collapsible pump, a compressible pump, a foaming pump, or a spray pump.

Optionally, the hand sanitization device may further comprise one or more pump support positioned adjacent to the actuatable pump to provide stabilization and restrict lateral movement of the actuatable pump.

Optionally, the housing may comprise an upper housing portion, a lower housing portion, and a narrow housing portion therebetween. The handle may comprise a rose. The housing may be configured to be mounted on the door such that the upper housing portion lies above the rose, the lower housing portion lies below the rose, and the narrow housing portion lies adjacent the rose. The housing may be sized and shaped to avoid pinching the user's hand between the handle and the housing. The cartridge may comprise an upper cartridge portion, a lower cartridge portion, and a narrow cartridge portion therebetween which may be shaped substantially similarly to the upper housing portion, lower housing portion, and narrow housing portion, respectively.

In another aspect, a hand sanitization system is provided. The hand sanitization system comprises a door, a dispenser, and a door sensor. The door comprises a first side with a first handle and a second side with a second handle. The dispenser contains a sanitizer agent and is mounted on the first side of the door above the first handle. The door sensor is operably coupled to the dispenser and is configured to detect a presence of a user's hand on the first handle. The door sensor is configured to detect when the door is opened from the first side by detecting a user's hand on the first handle. The door sensor is configured not to detect when the door is opened from the second side by actuation of the second handle.

Optionally, the door sensor may comprise an infra-red sensor configured to emit a beam of infra-red radiation to a pre-determined point. The pre-determined point may be one or more of above, behind, or in front of the first handle.

Optionally, the device may further comprise a control circuit configured to collect data, collate data, or transmit data. The data may comprise one or more of a drip event, a door opening event, a sanitization event, or a ratio of sanitization events to door opening events for a pre-determined number of users.

Optionally, the door may comprise a latched door, a locking door, an automatic door, a door operated by a switch, or an emergency door.

Optionally, the hand sanitization system may further comprise a user interface system the user interface system comprising an indicator element, wherein the user interface system is configured to encourage the user to sanitize their hands. The indicator element may comprise one or more of a display, a colored light, or a plurality of colored lights.

Optionally, the hand sanitization system may further comprise an accelerometer configured to detect movement of the door. The accelerometer may be configured to detect a door opening event when movement of the door is detected. The accelerometer may be configured to activate one or more of a user interface system or a door sensor when movement of the door is detected.

Optionally, the hand sanitization system may further comprise a proximity sensor configured to sense the user approaching the door. The proximity sensor may be configured to activate one or more of a user interface system or a door sensor when an approaching user is sensed.

Optionally, the door sensor may comprise an infra-red sensor configured to emit a beam of infra-red radiation to a pre-determined point. The pre-determined point may be located above, behind, or in front of the handle.

Optionally, the hand sanitization system may further comprise a control circuit configured to collect data, collate data, or transmit data. The data may comprise a drip event, a door opening event, a sanitization event, or a ratio of sanitization events to door opening events for a pre-determined number of users.

In another aspect, a method for promoting hand sanitization is provided. The method comprises sensing a user approaching a door, the door comprising a handle, activating a user interface system when the user approaches the door, when the user's hand grips the handle, or when the door moves, the user interface system comprising an indicator element and configured to encourage the user to sanitize their hands, dispensing a sanitizer agent from a hand sanitization device mounted on the door when the user's hand operates an actuation mechanism of the hand sanitization device, recording a hand sanitization event when the user's hand operates the actuation mechanism of the hand sanitization device, sensing when a user's second hand grips the handle, and recording a door opening event when the user's second hand opens the door by gripping the handle without recording a door opening event if the door is opened without the user's second hand gripping the handle.

Optionally, sensing the approaching user may comprise sensing the user using a proximity sensor coupled to a control circuit of the hand sanitization device.

Optionally, the indicator element may comprise one or more of a display, a colored light, or a plurality of colored lights. The user interface system may change one or more of a color of the one or more colored lights, an image displayed by the display, or a statistic displayed by the display as the user moves closer to the door.

Optionally, dispensing the sanitizer agent may occur independently of door opening.

Optionally, dispensing the sanitizer agent may comprise moving the actuation mechanism from a first position to a second position.

Optionally, the method may further comprise detecting movement of the door with an accelerometer coupled to a control circuit of the hand sanitization device.

Optionally, the method may further comprise detecting when the user's hand grips the handle with a door sensor operably coupled to the hand sanitization device. The door sensor may comprise an infra-red sensor configured to emit a beam of infra-red radiation to a pre-determined point. The pre-determined point may be located above, behind, or in front of the handle. Detecting when the user's hand grips the handle may comprise detecting reflectance of the infra-red radiation off of the user's hand when the user's hand comes between the door sensor and the pre-determined point so as to break the beam.

Optionally, activating the user interface system may comprise projecting one or more images designed to encourage the user to use the hand sanitization device.

Optionally, the method may further comprise recording a drip event when the sanitizer agent is dispensed.

Optionally, the method may further comprise collecting data, collating data, or transmitting data. The data may comprise a drip event, the door opening event, the hand sanitization event, or a ratio of hand sanitization events to door opening events for a pre-determined number of users.

In another aspect, a method for promoting hand sanitization is provided. The method comprises dispensing a sanitizer agent from a hand sanitization device mounted on a door comprising a handle when a user's hand operates an actuation mechanism of a hand sanitization device, recording a hand sanitization event when the user's hand operates the actuation mechanism of the hand sanitization device, sensing when a user's second hand grips the handle, recording a door opening event when the user's second hand opens the door by gripping the handle without recording a door opening event if the door is opened without the second hand of the user gripping the handle, and calculating the ratio of hand sanitization events to door opening events for a pre-determined number of users.

Optionally, the method may further comprise displaying the ratio of hand sanitization events to door opening events to the user.

Optionally, the method may further comprise detecting movement of the door with an accelerometer coupled to the hand sanitization device.

Optionally, the method may further comprise activating a user interface system prior to dispensing the sanitizer agent, the user interface system comprising an indicator element, wherein the indicator element comprises a display, a colored light, or a plurality of colored lights, and wherein the user interface system is configured to encourage the user to sanitize their hands. Optionally, the method may further comprise changing one or more of a color of the one or more colored lights, an image displayed by the display, or a statistic displayed by the display of the user interface system. Alternatively or in combination, activating the user interface system may comprise projecting one or more images designed to encourage the user to use the hand sanitization device.

Optionally, dispensing the sanitizer agent may occur independently of door opening.

Optionally, dispensing the sanitizer agent may comprise moving the actuation mechanism from a first position to a second position.

Optionally, the method may further comprise detecting movement of the door with an accelerometer coupled to a control circuit of the hand sanitization device.

Optionally, the hand sanitization device may comprise an infra-red sensor configured to emit a beam of infra-red radiation to a pre-determined point. The pre-determined point may be located above, behind, or in front of the handle. Sensing when the user's hand grips the handle may comprise detecting reflectance of the infra-red radiation off of the user's hand when the user's hand comes between the infra-red sensor and the pre-determined point so as to break the beam.

Optionally, the method may further comprise recording a drip event when the sanitizer agent is dispensed.

Optionally, the method may further comprise collecting data, collating data, or transmitting data. The data may comprise a drip event, the door opening event, the hand sanitization event, or a ratio of hand sanitization events to door opening events for a pre-determined number of users.

In another aspect, a hand sanitization device is provided. The hand sanitization device comprises a housing configured to be mounted on a door comprising a handle. The handle comprises a rose. The housing is configured to be mounted on the door such that an upper housing portion lies above the rose, a lower housing portion lies below the rose, and a narrow housing portion lies adjacent the rose. A cartridge containing sanitizer agent and an actuatable pump are disposed within the housing. The cartridge is operably coupled to the actuatable pump such that actuation of the actuatable pump causes the cartridge to dispense the sanitizer agent to a user's hand. An actuation mechanism is operably coupled to the actuatable pump and movable from a first position to a second position. Movement of the actuation mechanism from the first position to the second position actuates the pump.

Optionally, the cartridge may comprise an upper cartridge portion, a lower cartridge portion, and a narrow cartridge portion therebetween which are shaped substantially similarly to the upper housing portion, lower housing portion, and narrow housing portion, respectively, so that the cartridge may be disposed in the housing.

Optionally, the hand sanitization device may further comprise a pump sheath adjacent the pump and coupled to the cartridge. The pump sheath may act to protect internal components in the housing from being splashed by the sanitizer agent when dispensed from the pump.

Optionally, the housing may be sized and shaped to avoid pinching the user's hand between the handle and the housing.

In another aspect, a hand sanitization system is provided. The hand sanitization system comprises a hand sanitization device and a door comprising a handle. The handle comprises a rose. The hand sanitization device is mounted on the door such that the upper housing portion lies above the rose, the lower housing portion lies below the rose, and the narrow housing portion lies adjacent the rose, the dispenser containing a sanitizer agent.

Optionally, the housing may be sized and shaped to avoid pinching the user's hand between the handle and the housing.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3A depicts a front elevation view of another device to promote hand sanitization mounted on a door, in accordance with embodiments;

FIG. 3B depicts a side elevation view of the device of FIG. 3A, in accordance with embodiments;

FIG. 3C depicts a plan view of the device of FIG. 3A, in accordance with embodiments;

DETAILED DESCRIPTION OF THE INVENTION

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments, however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Figure 1:
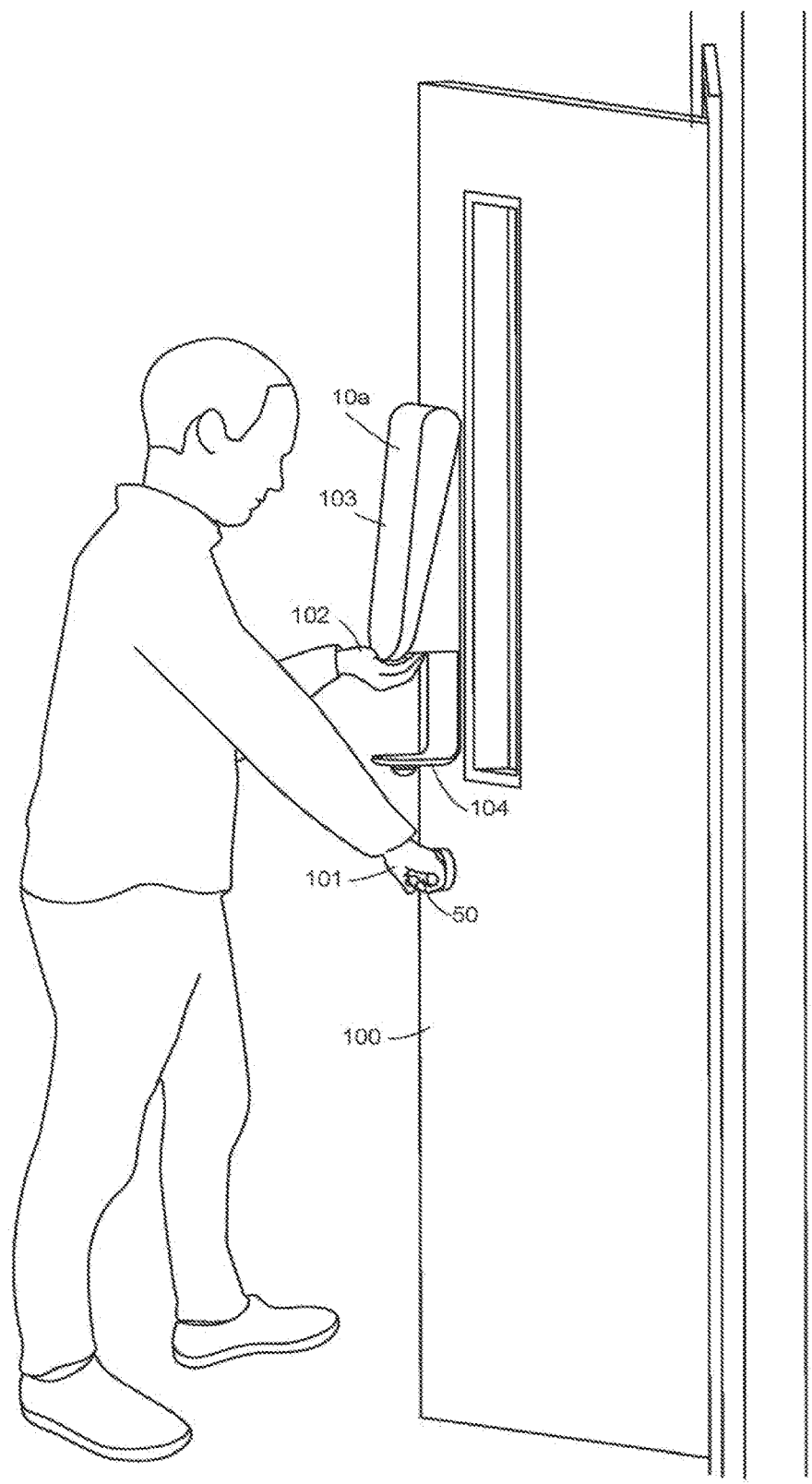
FIG. 1 depicts a perspective view of a device to promote hand sanitization mounted on a door, in accordance with embodiments.

FIG. 1 depicts a perspective view of a dispenser device 10a to promote hand sanitization mounted on a door. The dispenser 10a may be mounted on to a door 100. The door 100 may alternatively comprise any door, for example a latched door, a locking door, an automatic door, a door operated by a switch, an emergency door, or the like. The door 100 may be in a hospital or other medical facility, for example a door used to access or exit an operating room, a delivery room, a patient examination room, a restroom, or the like. The door 100 may be in any area or building where cleanliness is important, for example in food manufacturing or processing, in a restaurant, on a cruise ship, or in a military facility. Alternatively, the dispenser 10a may for example be mounted onto a piece of medical equipment comprising a handle or latch, for example an oven, an autoclave, a refrigerator, a freezer, or the like. The door 100 may comprise any thickness and may comprise a lock or locking system. The locking mechanism may for example comprise one or more of a magnet, a plurality of magnets, an electrical circuit or system, or any other mechanism known in the art. The door 100 may comprise a handle 50 which may for example be one or more of a latched handle, an anti-ligature handle, a wide-grip handle, a paddle, a grip bar, a push button, a push plate, a lever handle, a push handle, a pull handle, a door knob, a crashbar handle, a hospital latch, or the like. The dispenser 10a may be configured to be mounted on any type of door comprising any type of handle. In this way, the dispenser 10a may be fitted to a wide range of doors and thereby provide increased utility and ease of deployment in a variety of settings. The dispenser 10a may be mounted by one or more of many mechanisms including for example screws and bolts, rivets, adhesives, or any combination thereof.

The door 100 may comprise a latched door, for example, which is kept closed by a latched, turning lever handle 50. The dispenser 10a may be mounted onto the door 100 such that an optional drip tray 104, which may be located at the end of the dispenser 10a nearest the handle 50, is positioned at a set distance above the handle 50. A first hand 101 of a user may grip and turn or otherwise actuate the handle 50 so as to open the door 100. The door 100 may for example be pushed away from the user or pulled toward the user, depending on the opening mechanism of the door 100 to which the dispenser 10*a* is attached. A second hand 102 of the user may be used to operate the dispenser device 10*a*. The dispenser 10*a* may be configured such that sanitizer dispensing is independent of handle 50 operation and door 100 opening. Contrary to conventional wisdom, many users need the option to opt out of sanitization when passing through a door. For example, doctors and nurses moving quickly or carrying important samples or documents may prefer to opt out of sanitization rather than interrupt their travel or risk getting sanitizer fluid on critical items. The second hand 102 may be used to push or pull on an actuating mechanism 103. The actuation mechanism 103 may for example comprise a moveable panel, a moveable arm, a lever, a switch, a button, a wedge, a knob, a pull, a solenoid, a sensor (e.g. infra-red or ultrasound) in combination with a solenoid, or the like. The actuation mechanism 103 may be sized and shaped such that it protrudes outwards from the door 100 in order to allow sufficient space below and/or behind the arm 103 for the hand 102 to operate the mechanism 103 without pinching the fingers of the user. The second hand 102 may be positioned with the palm up above the drip tray 104 but under the actuation mechanism 103. The heel of the hand 102 may press on the actuation mechanism 103 to activate the dispenser 10*a* and provide a sanitizer agent into the waiting palm of the second hand 102. Alternatively, the fingers may be used to draw the actuation mechanism outwardly away from the door to actuation the dispenser to provide sanitizer agent into the cupped hand. The upside down v-shape of the actuation mechanism as shown here may facilitate proper hand placement as described herein, which may help prevent spillage of the sanitizer agent on the floor or other surfaces below the dispenser 10*a*. Further, the drip tray 104 may be used to capture any sanitizer agent which does not reach the hand 102. The dispenser 10*a* may be positioned such that the hand 102 is able to operate the dispenser 10*a* without undue effort (e.g. crossing arms/hands, reaching too high, reaching too low, etc.) in operating either the handle 50 or the device 10*a* for a majority of users. The user may be able to operate the dispenser 10*a* before, during, or after actuation of the handle 50 and opening of the door 100.

Alternatively or in combination, the actuation mechanism 103 may automatically dispense the sanitizer agent into the palm of the second hand 102 without contact between the hand 102 and the actuation mechanism 103. The dispenser 10*a* may for example comprise a sensor configured to detect the presence of the hand 102 above the drip tray 104 or below the actuating mechanism 103. The sensor may signal for the actuation mechanism 103 to be automatically activated. In this way, the user's hand may operate the actuation mechanism 103 without directly contacting the actuation mechanism 103. The sensor may be substantially similar to any of the sensors described herein. The actuation mechanism 103 may be located on an external portion of the dispenser 10*a* as illustrated or may be disposed within the body of the dispenser 10*a*. Actuation of the actuation mechanism 103 may cause the dispenser 10*a* to dispense sanitizer agent as described herein.

Figure 2:
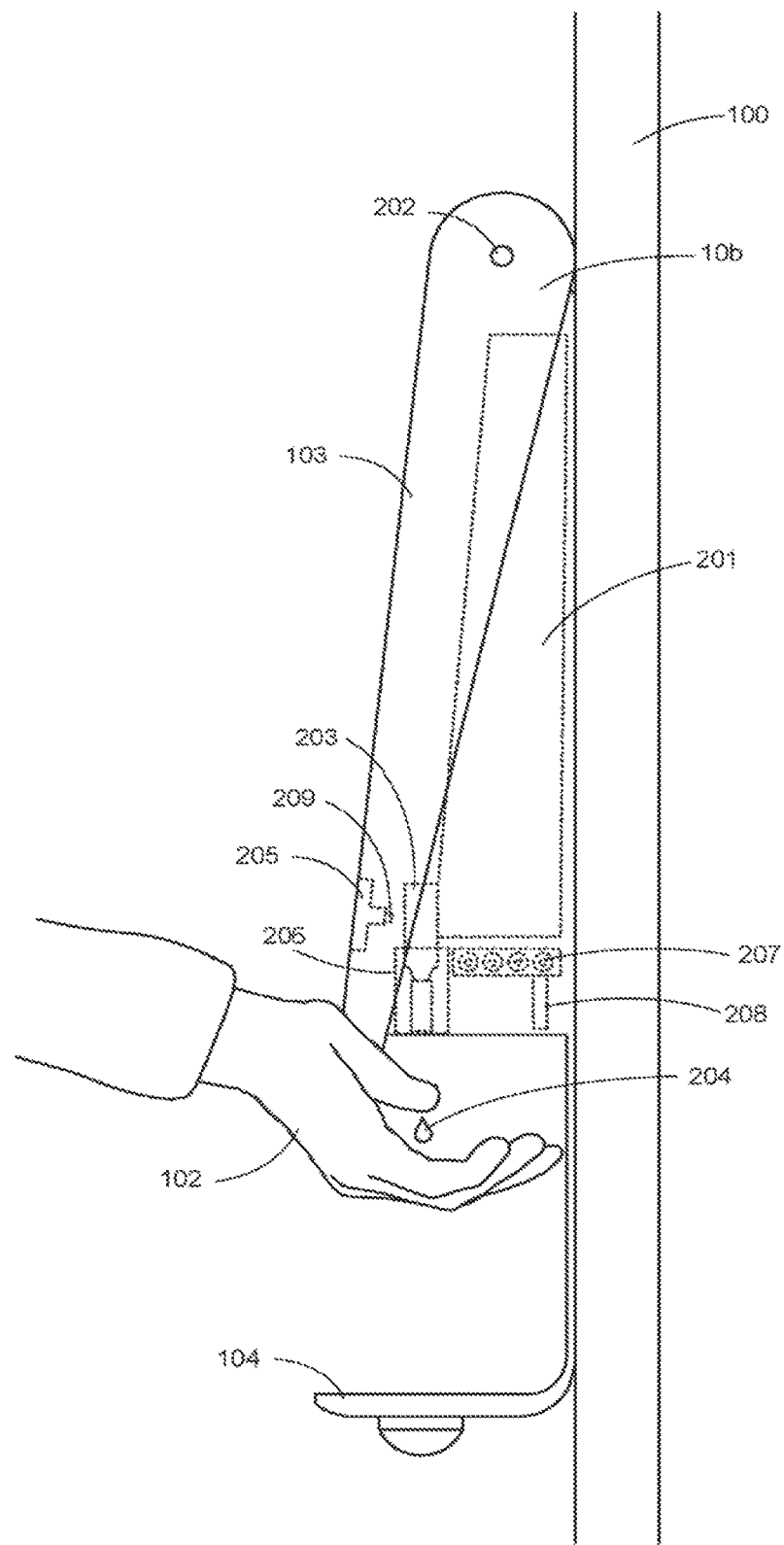
FIG. 2 depicts a side elevation view of a device to promote hand sanitization, in accordance with embodiments.

FIG. 2 depicts a side elevation view of a device 10*b* to promote hand sanitization. The dispenser 10*b* may be mounted on to a door 100 comprising a handle (not shown) as described herein. A second hand 102 of the user may be used to operate the dispenser device 10*b* by operating the actuation mechanism 103 as described herein. The device 10*b* may comprise a drip tray 104 positioned above the handle and used to capture sanitizer agent 204 which does not reach the hand 102 as described herein.

The actuation mechanism 103 may for example comprise a moveable arm or panel coupled by a hinge or pivot 202 to a housing body which contains the sanitizer dispensing mechanism. The housing may further contain a cartridge 201 containing sanitizer agent 204. The housing body may comprise any suitable material, for example a metal, a plastic, or the like, or combinations thereof. The sanitizer agent 204 may for example comprise an alcohol fluid, an alcohol gel, an alcohol foam, a fungicidal agent, a virucidal agent, a biocidal agent, or the like, or any combination thereof. The cartridge 201 may be one or more of removable, replaceable, or refillable. The cartridge 201 may comprise a volume of sanitizer agent or fluid 204 comparable to other dispensers known in the art, for example about 800 ml. The pivot 202 may be located on the upper end of the actuation arm 103 furthest from the handle of the door 100 and operably coupled to the lower end of the actuation mechanism 103 nearest the handle. Pushing on the lower end of the actuation mechanism 103 may cause rotation of the arm 103 about the pivot 202 and movement of the arm 103 towards the door 100. The actuation mechanism 103 may be biased, for example by a mechanical spring, to return to its initial position when the user's hand releases the lower end of the actuation mechanism 103.

The cartridge 201 may be accessed for example by pulling on the lower end of the actuation mechanism 103 so as to cause rotation of the arm 103 about the pivot 202 and movement of the arm 103 towards the user and upwards to expose the cartridge 201, for example to allow for replacement of an empty cartridge 201. Alternatively or in combination, the device 10*b* may comprise an access door on the actuation mechanism 103 or the housing body which may provide access to the cartridge 201 for replacement or maintenance.

The cartridge 201 may comprise an actuatable pump 203 in fluid communication with the cartridge 201. The actuatable pump 203 may for example be a collapsible pump, a compressible pump, a foaming pump, a spray pump, or the like. The pump 203 may for example be one such as disclosed in U.S. patent application Ser. No. 11/220,018, the entire contents of which are herein incorporated by reference. The pump 203 may for example be made of an elastomeric material, for example one or more of natural rubber, synthetic rubber, polybutadiene, a vinyl, or other compliant materials. The pump 203 may be positioned within the housing of the dispenser 10*b* between the sanitizer cartridge 201 and the actuating mechanism 103. An internal side of the actuating mechanism 103 may comprise a wedge 205 which may be brought into contact with the pump 203 by pressing on the arm 103 in order to compress the pump 203 and dispense sanitizer agent 204 into the hand 102. Pump support 206 may be positioned around or adjacent to the pump 203 between or below the cartridge 201 and the actuating mechanism 103 in order to provide stabilization and restrict lateral movement of the pump 203. Pump support 206 may comprise a plurality of pump supports. The pump 203 may be compressed against the pump support 206 by the wedge 205 on the actuation mechanism 103 in order to dispense sanitizer agent 204 into the hand 102. The pump 203 may be refilled with sanitizer agent 204 when the compression is released as the actuation mechanism 103 is biased back to its initial position after the user's hand is removed from the actuation mechanism 103.

The device 10b may further comprise optional circuitry which may be used to record when a "sanitization event" occurs, e.g. when a user has actuated the actuation mechanism 103. The wedge 205 may comprise a sanitization event sensor 209 in communication with a control circuit 208 powered by a battery 207. The battery 207 may for example be rechargeable, disposable, replaceable, or the like, or any combination thereof. The sensor 209 may for example comprise a mechanical switch, a magnetic switch (e.g. a Hall-effect switch), or the like. The sensor 209 may be located between the wedge 205 and the pump 203 such that the sensor 209 contacts the pump 203 when the hand 102 pushes on the actuation mechanism 103, thereby dispensing the sanitizer agent 204 and signaling to the control circuit 208 that a sanitization event has occurred. The sanitization event data may for example be time-stamped. The present disclosure thus describes an optional system present within the dispenser 10b, or any of the dispensers disclosed herein, that can record the number of people who have used the dispenser 10b.

The control circuit 208 may perform one or more of recording data (e.g. sanitization event data or other event data as described herein), collating data, or transmitting data. The collected data may for example be wirelessly transmitted by the control circuit 208 to a smart phone or other data recording device. The data may for example be transmitted using Near Field Communication (NFC), Bluetooth, Wi-Fi, or the like. The data may be relayed to a processor, for example the 'cloud', and/or uploaded to a website where it may be collated and presented. The presented data may be used to facilitate improved control of infections and spread of disease in the facility in which the device 10b is installed. The data may be collected, collated, and presented locally on the device 10b.

FIGS. 3A-3C depict a device 10c to promote hand sanitization mounted on a door 100. The device 10c may comprise one or more design features which facilitate placement on a door. The dispenser 10c may be mounted on to a door 100 comprising a handle 50 as described herein. The device 10c may be substantially similar to any of the embodiments described herein. FIG. 3A depicts a front elevation view of the dispenser 10c. The dispenser 10c may comprise a width small enough to be mounted on a door 100 comprising a window 301. For example, many hospital doors comprise view windows which allow the user to look at the other side of the door so as to avoid collisions with other people or objects upon opening the door 100. The window 301 may be substantially closer to the free edge of the door 100 than to the hinged edge of the door 100. The dispenser 10c may have a width which allows for mounting of the device 10c above the handle 50 between the window 301 and the free edge of the door 100, whereas standard dispensers are too large to be so positioned on a door 100 with a window 301 as shown. A larger, standard dispenser could perhaps be mounted on the door 100 between the window 301 and the hinged edge of the door 100, however such a mounting location would be less visible to the user and harder to use, for example requiring crossing of arms in order to operate both the door 100 and the device 10c. The small width of the device may further provide for positioning of the device directly over or close to the free edge of the door 100 at an angle relative to the handle 50, even on doors which do not have a window 301. A device with a larger width would require positioning closer to the hinged edge of the door 100 at an angle above the handle 50, making it much more difficult and inconvenient to use as described herein. For at least these reason, the smaller width design of the dispenser 10c may be a substantial improvement over other proposed devices. FIG. 3B depicts a side elevation view of the device 10c mounted on door 100 above handle 50. The dispenser 10c may have a depth much smaller than that of a standard sanitizer dispenser. The dispenser 10c may protrude from the mounting surface, for example door 100, much less than a standard dispenser, thereby preventing passers-by from inadvertently striking the device 10c or the device from striking the wall when the door 100 is fully opened. FIG. 3C depicts a plan view of device 10c mounted on door 100. The device 10c may comprise a small enough width and depth as described herein such that opening of the door does not result in the dispenser 10c striking the door frame 302, as indicated by the dashed line. Despite the small dimensions of the dispenser 10c, the device may be configured in such a way so as to contain a sanitizer agent cartridge of a standard size as described herein, thereby preventing the regular refilling often required by smaller sanitizer dispensers.

Figure 4:
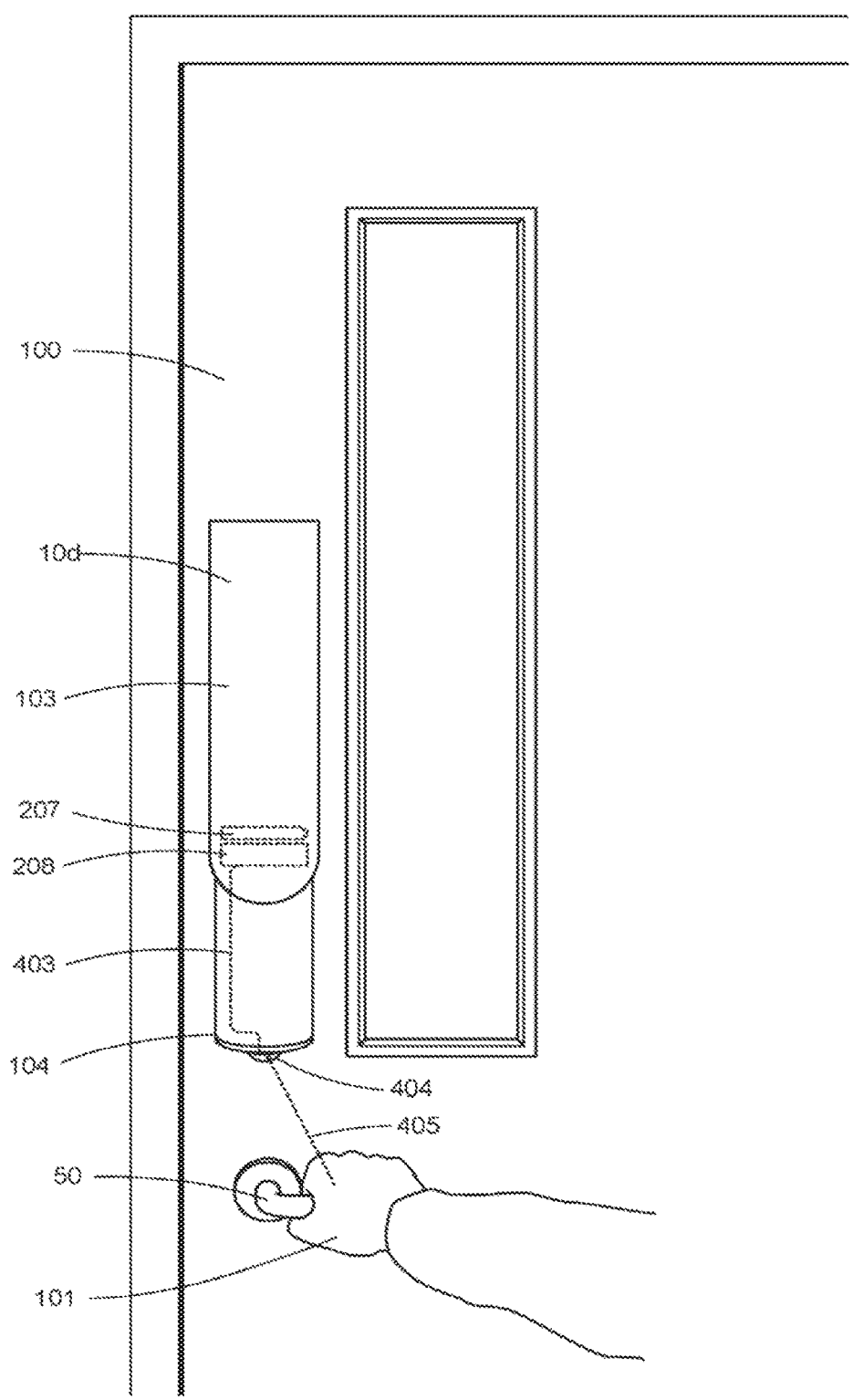
FIG. 4 depicts a front elevation view of a device to promote hand sanitization including a hand on the door handle, in accordance with embodiments.

FIG. 4 depicts a front elevation view of a device 10d to promote hand sanitization. The dispenser 10d may be mounted on to a door 100 comprising a handle 50 as described herein. The device 10d may comprise a cartridge (not shown) containing sanitizer agent as described herein. The cartridge may comprise an actuatable pump (not shown) in fluid communication with the cartridge as described herein. The device may comprise a small width and a small depth as described herein. A second hand (not shown) of the user may be used to operate the dispenser device 10d by operating the actuation mechanism 103 as described herein. The device 10d may comprise a drip tray 104 positioned above the handle 50 and used to capture sanitizer agent which does not reach the hand as described herein. The device 10d may comprise a battery 207 and control circuit 208 as described herein to collect, collate, and/or transmit data.

The device 10d may further comprise an optional electronic system to monitor the presence of a first hand 101 on the handle 50. Detection of a hand 101 on the handle 50 may be transmitted to the control circuit 208 via a wire 403 and recorded as a "door opening event". A door sensor 404 may be coupled to the lower end of the dispenser 10d, for example attached or integral to the underside of the drip tray 104 closest to the handle 50. The door sensor 404 may for example be an ultrasonic sensor or an infra-red (IR) detection device. The IR detection device 404 may for example be a modular IR device. The IR detection device 404 may be configured to emit a narrow beam or field of IR radiation 405 a set distance downward toward the handle 50, for example towards a point above, behind, and/or in front of the handle 50 as described herein. When the hand 101 grips the handle 50, the hand 101 may break the IR beam 405 and cause IR radiation to be reflected back towards the IR detection device 404. The reflected IR radiation may be detected by the IR detection device 404, which may then send a signal to the control circuit 208 which may be processed and recorded as a door opening event by the onboard electronic memory of the control circuit 208. The door opening event data may for example be time-stamped. The hand 101 may release the handle 50 as the user passes through the door 100, which may cause the IR radiation to no longer be reflected. Alternatively or in combination, the release of the handle 50 may be detected by the IR detection device 404 as an absence of IR reflection. The IR detection device may signal to the control circuit 208 that the door opening event has ended. Alternatively or in combination, the handle 50 may comprise a sensor operably coupled to the control circuit 208. The sensor on the handle 50 may for example use capacitive sensing, heat sensing, or pressure sensing to sense the presence of the hand 101 gripping the handle 50 and subsequently send a signal to the control circuit 208 which may be processed and recorded as a door opening event as described herein. The present disclosure thus describes an optional electronic system present within the dispenser 10d, or any of the dispensers disclosed herein, that can record the number of people operating and passing through the door 100.

Figure 5:
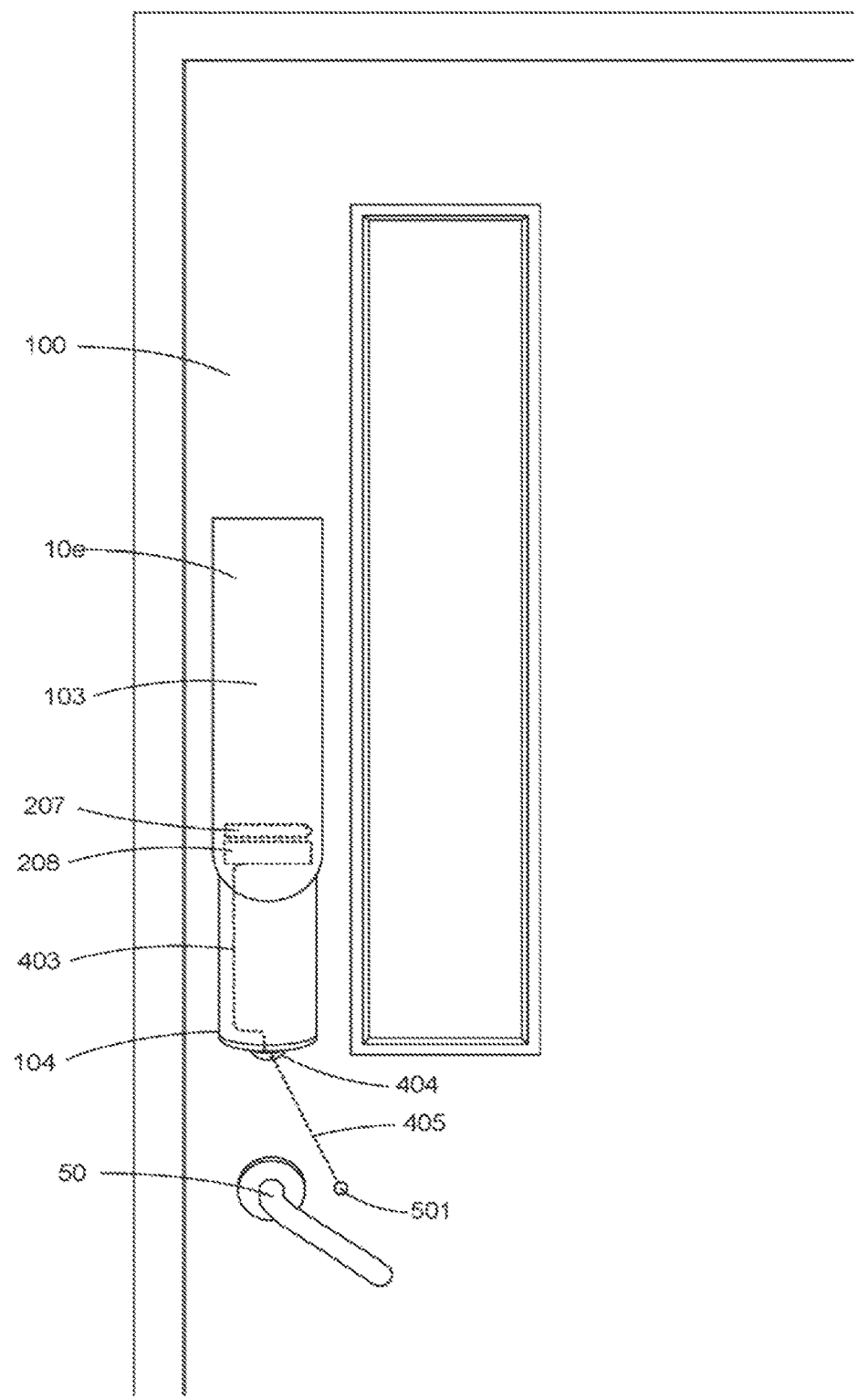
FIG. 5 depicts a front elevation view of a device to promote hand sanitization without a hand on the door handle, in accordance with embodiments.

FIG. 5 depicts a front elevation view of a device 10e to promote hand sanitization. The dispenser 10e may be mounted on to a door 100 comprising a handle 50 as described herein. The device 10e may comprise a cartridge (not shown) containing sanitizer agent as described herein. The cartridge may comprise an actuatable pump (not shown) in fluid communication with the cartridge as described herein. The door 100 may comprise a door which has handles 50 on a first side and a second opposite side of the door 100. The dispenser 10e may be mounted on a first side of the door 100. Alternatively or in combination, the dispenser 10e may be mounted on an opposite side of the door 100. For example, in some embodiments, each of the first side and the second side of the door 100 may have a dispenser 10e mounted thereupon. The device 10e may comprise a small width and a small depth as described herein. A second hand (not shown) of the user may be used to operate the dispenser device 10e by operating the actuation mechanism 103 as described herein. The device 10e may comprise a drip tray 104 positioned above the handle 50 and used to capture sanitizer agent which does not reach the hand as described herein. The device 10e may comprise a battery 207 and control circuit 208 as described herein to collect, collate, and/or transmit data. The device 10e may be coupled to an IR detection device 404 connected to the control circuit 208 via a wire 403 as described herein. The IR detection device 404 may detect the presence of a hand on the handle 50 and record a door opening event as described herein.

The dispenser 10e may be mounted on a first side of the door 100 as described herein. The IR detection device 404 may be configured to emit an IR beam 405 downwards towards a point 501 above, behind, and/or in front of the handle 50 of the first side of the door 100. The IR detection device 404 may be configured such that a door opening event is recorded only when the door is opened by operation of the handle 50 on the first side of the door 100. When a hand is placed on the handle 50 of the first side of the door 100, the IR beam 405 terminating at point 501 may be broken by the hand, causing IR radiation to reflect back to the IR detection device 404 and causing a door opening event to be recorded as described herein. However, in the event that no hand is on the handle 50 of the first side of the door 100, for example when the handle 50 of an opposite side of the door 100 is actuated, the IR beam 405 terminating at point 501 above, behind, and/or in front of the handle 50 on the first side of the door 100 may remain unbroken as shown, therefore no door opening event may be recorded. In this way, the dispenser 10e may distinguish between a user opening the door 100 from the opposite site and a user opening the door 100 from the first side on which the dispenser 10e is mounted. In this way, the dispenser 10e may be configured to limit its count of door opening events to those which are initiated by the handle 50 on the same side of the door 100 as the dispenser 10e is mounted.

Alternatively or in combination, the handle 50 on the first side of the door 100 may comprise a sensor operably coupled to the control circuit 208. The handle 50 on the opposite side of the door 100 may not comprise a sensor. The sensor on the first handle 50 may for example use capacitive sensing or heat sensing to sense the presence of the first hand gripping the handle 50 and subsequently send a signal to the control circuit 208 which may be processed and recorded as a door opening event as described herein. When the door 100 is opened from the opposite side, the sensor on the handle 50 on the first side does not detect the presence of the user's hand and therefore may not record a door opening event. Thus, the dispenser 10e may be distinguish between operation of the handle 50 on the first side of the door 100 on which the dispenser 10e is mounted and operation of the second handle 50 on the opposite side of the door 100. The present disclosure thus describes an optional electronic system present within the dispenser 10e, or any of the dispensers disclosed herein, that can record the number of people operating and passing through the door 100 from the side on which the dispenser 10e is mounted.

Figure 6:
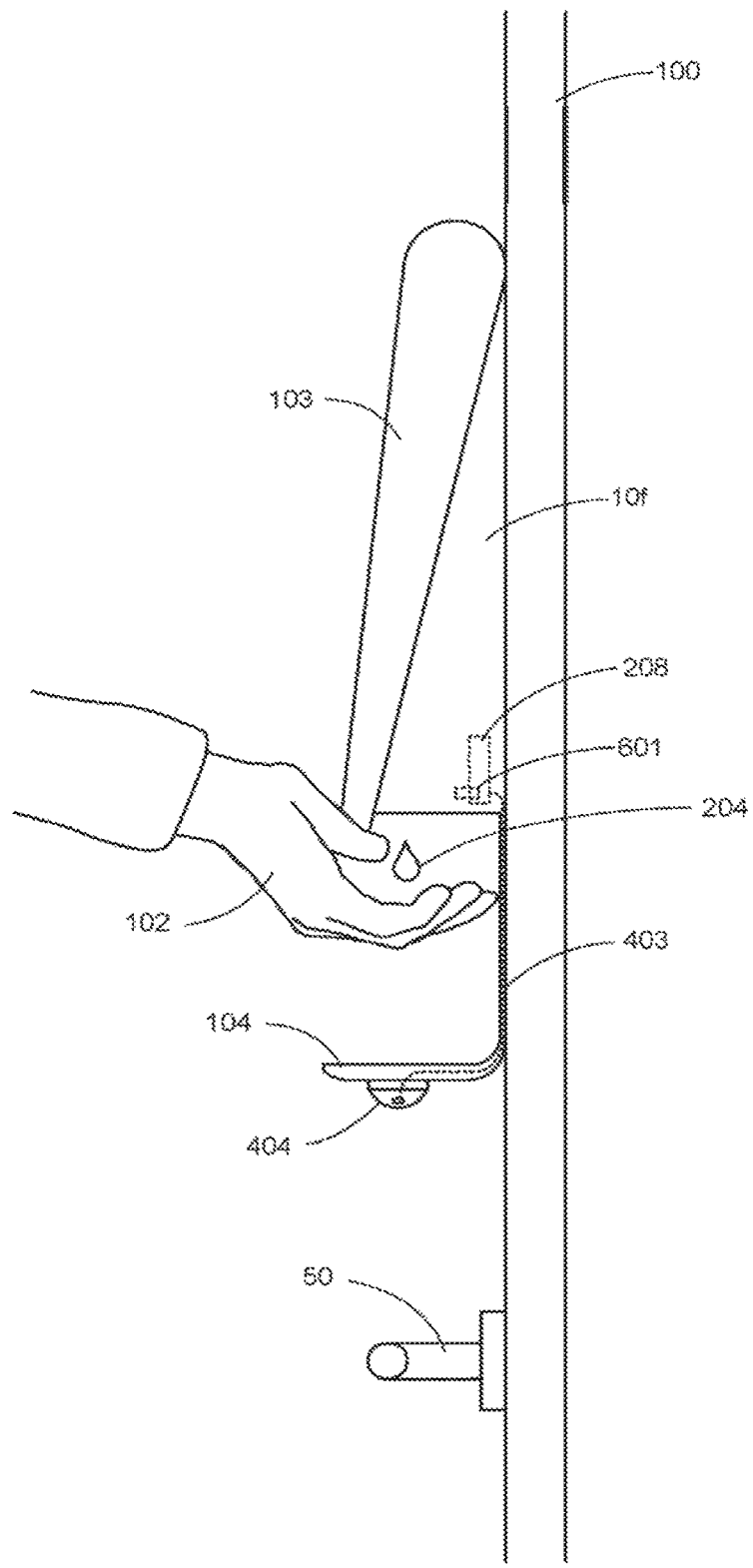
FIG. 6 depicts a side elevation view of yet another device to promote hand sanitization, in accordance with embodiments.

FIG. 6 depicts a side elevation view of yet another device to promote hand sanitization. The dispenser 10f may be mounted on to a door 100 comprising a handle 50 as described herein. The device 10f may comprise a cartridge (not shown) containing sanitizer agent as described herein. The cartridge may comprise an actuatable pump (not shown) in fluid communication with the cartridge as described herein. The device may comprise a small width and a small depth as described herein. A second hand 102 of the user may be used to operate the dispenser device 10f by operating the actuation mechanism 103 to dispense a sanitizer agent 204 as described herein. The device 10f may comprise a drip tray 104 positioned above the handle 50 and used to capture sanitizer agent 204 which does not reach the hand 102 as described herein. The device 10f may comprise a battery (not shown) and control circuit 208 as described herein to collect, collate, and/or transmit data. The device 10f may be coupled to an IR detection device 404 connected to the control circuit 208 via a wire 403 as described herein. The IR detection device 404 may detect the presence of a hand (not shown) on the handle 50 and record a door opening event as described herein. The IR detection device 404 may be configured to record a door opening event when the handle 50 below the device 10f is actuated by a hand on the handle 50, and to not record a door opening event when the handle 50 is actuated in on the opposite side of the door as described herein.

The device 10f may further comprise an optional accelerometer 601 coupled to the control circuit 208. The accelerometer 601 may be mounted on or otherwise attached to the control circuit 208 within the housing of the device 10f. The accelerometer 601 may be used to activate the IR detection device 404 via wire 403 when movement of the door 100 is detected by the accelerometer 601. The IR detection device 404 may be configured to remain inactive, e.g. configured not to emit an IR beam, until movement of the door 100 is detected in order to drastically save on power consumption. Thus, when the device 10f is used solely for the purpose of acquiring hand sanitizer 204, the IR detection device 404 remains in standby mode and little power is consumed. In some embodiments, the accelerometer 601 may signal to the control circuit 208 that a door opening event has occurred. The accelerometer 601 may be used in tandem with the IR detection device 404 to determine if a door opening event has occurred. Standard automatic sanitizer dispensers are typically configured to remain always on or cycle their sensors, which may lead to excessive power consumption, whereas the IR detection device 404 is only on when the door 100 is in use. The present disclosure thus describes an optional electronic system present within the dispenser 10f, or any of the dispensers disclosed herein, that can record the number of people operating and passing through the door 100 while drastically saving on power consumption.

Figure 7:
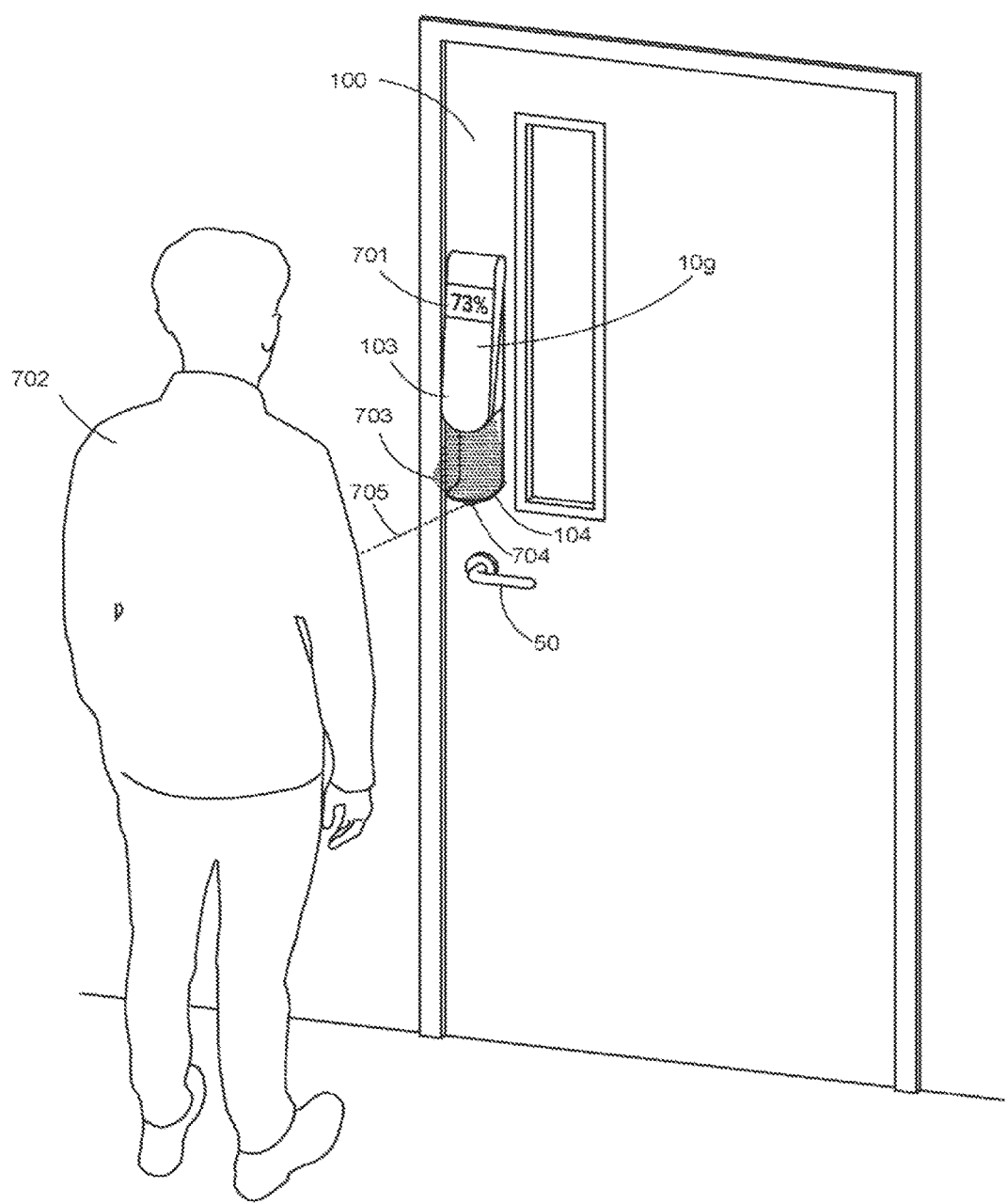
FIG. 7 depicts a perspective view of a device to promote hand sanitization comprising a proximity sensor and user interface, in accordance with embodiments.

FIG. 7 depicts a perspective view of a device 10g to promote hand sanitization. The dispenser 10g may be mounted on to a door 100 comprising a handle 50 as described herein. The device 10g may comprise a cartridge (not shown) containing sanitizer agent as described herein. The cartridge may comprise an actuatable pump (not shown) in fluid communication with the cartridge as described herein. The device 10g may comprise a small width and a small depth as described herein. A second hand (not shown) of the user 702 may be used to operate the dispenser device 10g by operating the actuation mechanism 103 to dispense a sanitizer agent as described herein. The device 10g may comprise a drip tray 104 positioned above the handle 50 and used to capture sanitizer agent which does not reach the hand as described herein. The device 10g may comprise a battery (not shown) and control circuit (not shown) as described herein to collect, collate, and/or transmit data.

The device 10g may further comprise an optional user interface system configured to interact with the user 702. The device 10g may comprise a sensor 704, for example a proximity sensor, which may activate one or more user interface components upon detection of an approaching user 702. The proximity sensor 704 may be coupled to the drip tray 104. The proximity sensor 704 may for example be an infrared sensor or an ultrasonic sensor. The proximity sensor 704 may for example emit an IR beam 705 projected outwards from the door 100, for example approximately perpendicular to the plane of the door 100. When a user 702 interrupts the IR beam 705, IR radiation may be reflected back to the proximity sensor 704. The proximity sensor 704 may trigger one or more user interface components. The user interface may comprise an indicator element. The indicator element may comprise a display 701, one or more colored lights 703, or any combination thereof. One or more indicator element may be configured to encourage the user 702 to sanitize their hands as they operate the door 100. The one or more indicator element may for example be located on the device 10g so as to draw the gaze of the user 702 towards the proper location for placing their hand on the device 10g, such as near the lower end of the actuation mechanism 103.

Alternatively or in combination, the optional accelerometer (not shown) described herein may be used to detect the user 702 and/or activate one or more components of the user interface system, for example one or more indicator element, when movement of the door 100 is detected by the accelerometer. The one or more indicator elements, for example one or more colored lights 703, may be configured to remain inactive, e.g. configured not to emit colored light, until movement of the door 100 is detected in order to save on power consumption. In some embodiments, the accelerometer may signal to the optional control circuit (not shown) that a door opening event has occurred.

The display 701 may be located at about eye level on the actuation mechanism 103. The display 701 may be activated to display information to the user 702, for example information pertaining to hand sanitization such as the percentage of users passing through the door who have sanitized their hands. The device 10g may thereby benefit from a human psychology of shared social responsibility where information about use by other users encourages an approaching user 702 to also sanitize their hands for the benefit of all users in the form of reduced risk of infection. For example, a low percentage of users displayed may encourage the approaching user 702 to use the device 10g in order to increase the percentage displayed by the display 701. Similarly, a high percentage of users displayed may encourage the approaching user 702 to use the device 10g in order to maintain a high percentage rather than opt out and contribute to a reduction in the use percentage. The display 701 may for example flash the sanitization rate as the user 702 approaches the door 100 in order to direct the gaze of the user 702 towards the display 701.

Alternatively or in combination, one or more colored lights 703 may be used to encourage an approaching user 702 to use the device 10g and sanitize their hands. The one or more colored lights 703 may for example comprise one or more light emitting diodes (LEDs). One or more LEDs (not shown) may be mounted to the underside of the housing of the dispenser 10g or within the housing of the dispenser 10g. The LEDs may project colored light 703 down towards the drip tray 104 in order to catch the attention of the user 702 and direct the gaze of the user 702 to the device 10g, thereby reminding the user 702 to sanitize their hands. Alternatively or in combination, the one or more LEDs may be mounted on or within the housing of the dispenser 10g, for example on or behind the actuation mechanism 103. The LEDs may project colored light from or through the actuation mechanism 103 (wherein the actuation mechanism may comprise a material at least partially transmissive to the light from the LEDs) in order to catch the attention of the user 702 and direct the gaze of the user 702 toward the actuation mechanism 103, thereby reminding the user 702 to sanitize their hands. The LEDs may for example be located on the device 10g so as to draw the gaze of the user 702 towards the proper location for placing their hand on the device 10g, such as near the lower end of the actuation mechanism 103. The color of the light 703 may remain the same as the user approaches the door 100. The color of the light 703 may change as the user approaches the door 100. Alternatively or in combination, the color of the light 703 may change as the user initiates a sanitization event (e.g. actuates the actuation mechanism 103) and/or a door opening event (e.g. operates the handle 50 and opens the door). For example, the one or more LEDs may initially project a green light 703 upon sensing the approaching user 702 with the proximity sensor 704 (or, alternatively or in combination, upon detecting movement of the door 100 with the accelerometer). As the user 702 gets closer to the door, the color of the light 703 may change to red to indicate to the user 702 the seriousness of the need to use the device 10g and sanitize their hands. In another example, the light 703 may initially be red to alert the user 702 to the need to use the device and then change to green when the device 10g is used and a sanitization event is recorded. In yet another example, the light 703 may initially be a neutral color, for example blue, in order to grab the attention of the approaching user 702. When the actuation arm 103 is pushed, the light 703 may switch to green in order to reward the user with a positive color and alert others nearby that the user 702 has sanitized their hands and helped reduce infections. If the user 702 opens the door 100 without using the device 10g, the light 703 may turn red, for example a flashing red, to further encourage the user 702 to sanitizer their hands. A red light 703 may also indicate to others nearby that the user has opted out of sanitization and is thereby promoting the spread of disease, thereby shaming the user and encouraging better future hand sanitization behavior. In some instances, the use of such lighting or display options as described herein as a behavioral cue to encourage users to sanitize their hands may be more effective than simply displaying the statistics of use on a display. For example, the use of flashing lights or projected images may draw the eye more readily to the sanitizer than a static statistical display, thereby reminding the user upon seeing the dispenser, which might otherwise have been overlooked, to sanitizer their hands.

In some instances, the one or more indicator elements of the user interface system may be non-visual. The indicator may comprise an audio indicator or cue, a tactile or touch indicator, or a smell indicator. For example, an audio cue may be triggered by movement of the door registered by the accelerometer. The audio cue may comprise a beep, a tone, a word, a phrase, a musical piece, a song, or other sound as desired by one of ordinary skill in the art which may draw the user's eye to the device 10g in order to remind the user to sanitizer their hands.

Any of the user interface components may be activated in sequence or in combination with any of the other user interface components described herein. The display 701 may be activated before, during, or after the one or more lights 703 are activated. The user interface components may be triggered at the same time or may be independently triggered. The display 701 may display data, an image, or a combination thereof. The display 701 may be constant or may flash to draw the attention of the user. The display 701 may turn on upon detection of the approaching user 702 by the proximity sensor 704. The display 701 may turn on or alter what it displays upon detection of a hand on the handle 50. The one or more lights 703 act in any permutation of the manners described herein. The lights 703 may be solid or flashing, may remain a single color or may alternate between multiple colors, or any combination thereof. The lights 703 may be any color in any order desired. It will be understood by one skilled in the art that any combination of display or lighting options may be utilized to encourage approaching users 702 to sanitize their hands. The present disclosure thus describes a user interface system present within the dispenser 10g, or any of the dispensers disclosed herein, that can encourage users to sanitize their hands using a user interface such as those described herein.

Figure 8:
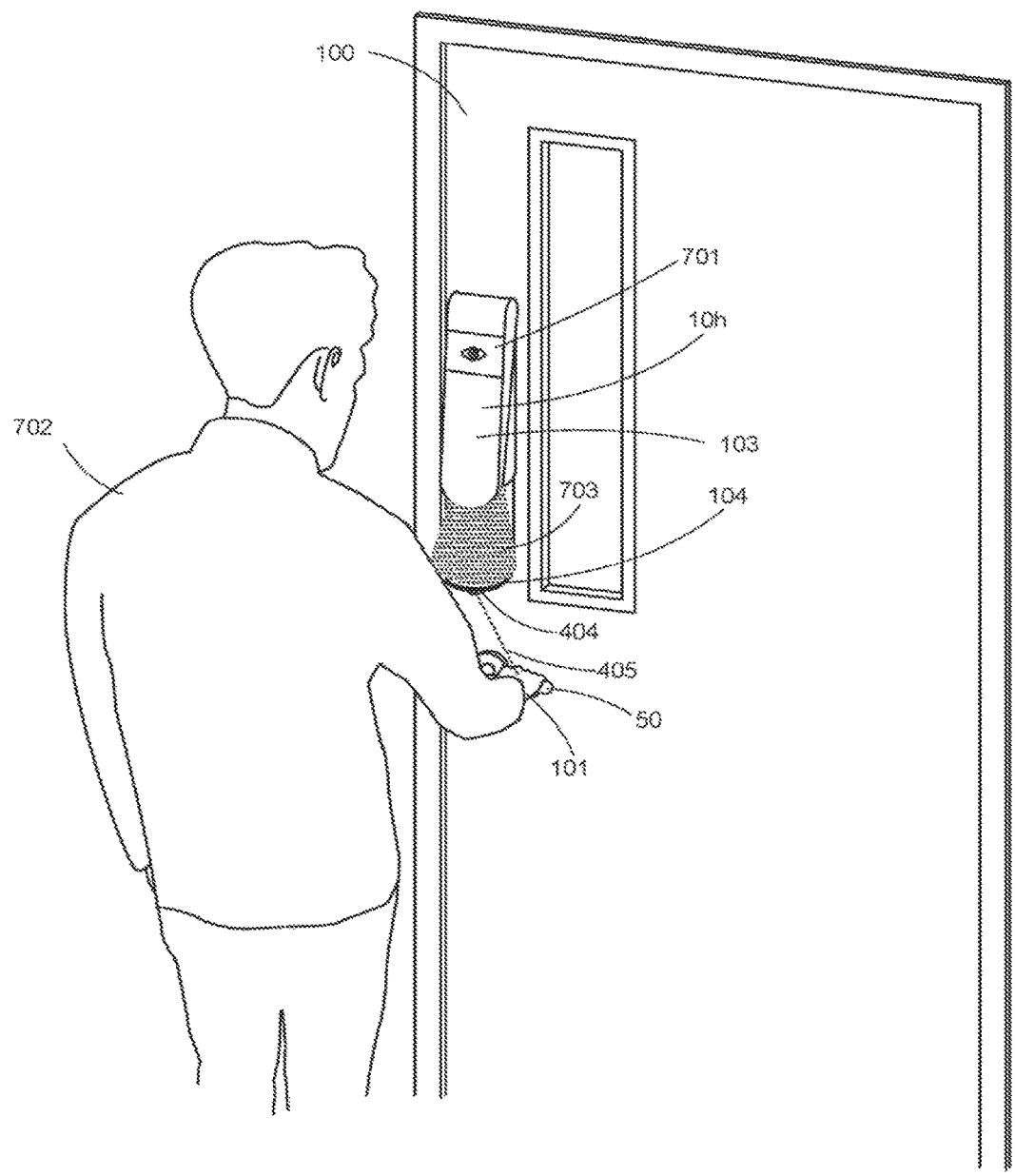
FIG. 8 depicts a perspective view of another device to promote hand sanitization comprising a proximity sensor and user interface, in accordance with embodiments.

FIG. 8 depicts a perspective view of a device 10h to promote hand sanitization. The dispenser 10h may be mounted on to a door 100 comprising a handle 50 as described herein. The device 10h may comprise a cartridge (not shown) containing sanitizer agent as described herein. The cartridge may comprise an actuatable pump (not shown) in fluid communication with the cartridge as described herein. The device 10h may comprise a small width and a small depth as described herein. A second hand (not shown) of the user 702 may be used to operate the dispenser device 10h by operating the actuation mechanism 103 to dispense a sanitizer agent as described herein. The device 10h may comprise a drip tray 104 positioned above the handle 50 and used to capture sanitizer agent which does not reach the hand as described herein. The device 10h may comprise a battery (not shown) and control circuit (not shown) to collect, collate, and/or transmit data as described herein. The device 10h may be coupled to an IR detection device 404 connected to the control circuit via a wire (not shown) as described herein. The IR detection device 404 may detect the presence of a hand 101 on the handle 50 with an IR beam 405 and record a door opening event as described herein. The IR detection device 404 may be configured to record a door opening event when the handle 50 below the device 10h is actuated by a hand 101 on the handle 50, and to not record a door opening event when the handle 50 is actuated in on the opposite side of the door 100 as described herein. The device 10h may comprise a user interface system as described herein. The device 10h may comprise a proximity sensor (not shown) which may activate one or more user interface components upon detection of an approaching user 702 as described herein. The user interface may comprise an indicator element, for example a display 701, one or more colored lights 703, or any combination thereof, as described herein. One or more user interface components may be configured to encourage the user 702 to sanitize their hands as they operate the door 100 as described herein.

The user interface system may be configured to project on the display 701 one or more images designed to encourage the user 702 to sanitize their hands. The one or more images may be displayed in response to detection of the approaching user 702 by the proximity sensor and/or in response to detection of a hand 101 on the handle 50 by the IR detection device 404. For example, a human eye may be displayed on the screen 701 when the user 702 grips the handle 50, as psychologists have found that images of eyes tend to make people more likely to follow rules. Alternatively or in combination, a downward pointing arrow may be displayed when the user 702 grips the handle 50 in order to indicate that recent use of the device 10h has been below expectations. Alternatively or in combination, a smiling face may be displayed when the user 702 operates the device 10h and sanitizes their hands. Alternatively or in combination, the display 701 may show a video, for example a short video instruction on how to actuate the actuation lever 103 to dispense sanitizer agent onto the hand. Alternatively or in combination, one or more lights 703 to encourage proper hand sanitization behavior as described herein. The present disclosure thus describes a user interface system present within the dispenser 10h, or any of the dispensers disclosed herein, that can encourage users to sanitize their hands.

Figure 9:
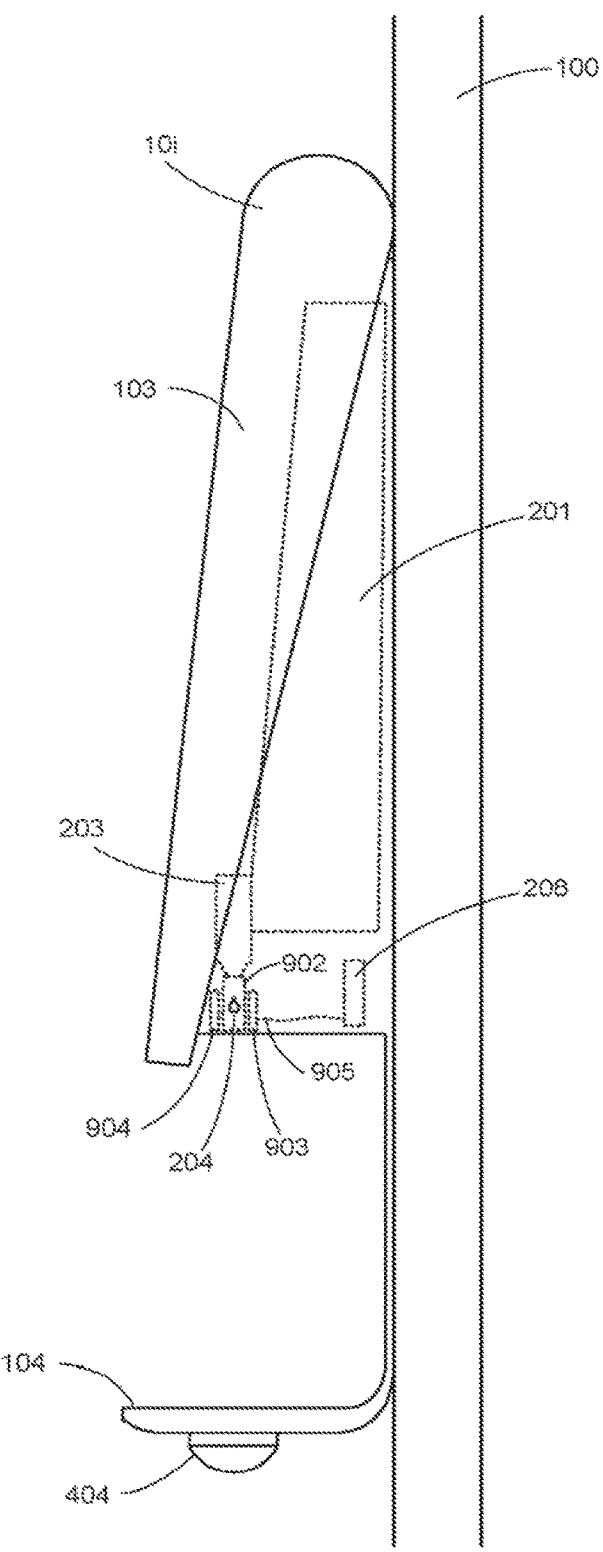
FIG. 9 depicts a side elevation view of a device to promote hand sanitization comprising a pump sheath, in accordance with embodiments.

FIG. 9 depicts a side elevation view of a device to promote hand sanitization. The dispenser 10i may be mounted on to a door 100 comprising a handle (not shown) as described herein. The device 10i may comprise a cartridge 201 containing sanitizer agent 204 as described herein. The cartridge 201 may comprise an actuatable pump 203 in fluid communication with the cartridge 201 as described herein. The device 10i may comprise a small width and a small depth as described herein. A second hand (not shown) of the user may be used to operate the dispenser device 10i by operating the actuation mechanism 103 to dispense a sanitizer agent 204 as described herein. The device 10i may comprise a drip tray 104 positioned above the handle and used to capture sanitizer agent which does not reach the hand as described herein. The device 10i may comprise a battery (not shown) and control circuit 208 to collect, collate, and/or transmit data as described herein. The device 10i may be coupled to an IR detection device 404 connected to the control circuit via a wire (not shown) as described herein. The IR detection device 404 may detect the presence of a hand the handle and record a door opening event as described herein.

The dispenser 10i may further comprise an optional sensor 903, for example a drip sensor, and IR reflector 904. The drip sensor 903 may comprise an IR detector. The drip sensor 903 may be connected to the control circuit 208 by a wire 905. The drip sensor 903 and IR reflector 904 may be placed on opposite sides of the dispensing path of the fluid 204. The drip sensor 903 may further comprise an IR emission device. An IR radiation beam (not shown) may be emitted from the drip sensor 903 towards the IR reflector 904. The IR beam may be reflected back on to the drip sensor 903 when there is no fluid 204 in the path of the IR beam. When the actuation mechanism 103 is pushed, the pump 203 may be compressed in order to cause sanitizer agent 204 to fall from the pump 203 towards on the hand of the user. As the drip or stream of sanitizer agent 204 falls from the pump 203, it may pass between the drip sensor 903 and IR reflector 904, thereby disrupting the reflection of the IR beam onto the drip sensor 903 and causing the drip sensor 903 to signal to the control circuit 208 that a "drip event" has occurred. The dispenser 10i may comprise one or more of a sanitization event sensor, hand detection device or door sensor, or accelerometer as described herein such that the recordation of a drip event may be correlated to a sanitization event, a door opening event, or any combination thereof. For example, the dispenser 10i may monitor for a sanitization event occurring without a drip event, indicating that the cartridge 201 is empty and in need of replacement. Alternatively or in combination, the dispenser 10i may monitor for a door opening event occurring with a drip event but without a sanitization event, which may indicate a leak in the cartridge 201 or pump 203. Alternatively or in combination, the dispenser 10i may monitor for a sanitization event occurring with a drip event, with or without a door opening event, which may indicate that the dispenser 10i is functioning properly. The present disclosure thus describes a drip sensor 903 within the dispenser 10i, or any of the dispensers disclosed herein, that may record when and if sanitizer agent 204 is dispensed by the dispenser 10i.

Alternatively or in combination the device 10i may comprise an optional pump sheath 902. The pump sheath 902 may be positioned adjacent the pump 203 such that the sanitizer agent 204 passes through the sheath 902 as it exits the dispenser 10i. The pump sheath 902 may be positioned or configured to protect liquid-sensitive components of the dispenser 10i from accidental splashes by the fluid 204 as it exits the dispenser 10i. The pump sheath 902 may for example be positioned between the drip sensor 903 and the IR reflector 904. The pump sheath 902 may comprise a tubular sheath. The pump sheath 902 may be part of the cartridge 201. The pump sheath 902 may for example be shaped so as to fit within a correspondingly shaped recess in the device 10i, for example in a shaped recess between the drip sensor 903 and the IR reflector 904, so as to act as a "key" to couple the cartridge to the device housing. The pump sheath 902 may be independent of the cartridge 201. The pump sheath 902 may be coupled to the housing of the device. The pump sheath 902 may comprise an optically or IR transparent or transmitting material such that the IR beam emitted by the drip sensor 903 may pass through the pump sheath 902 to the IR reflector 904 and back with minimal scattering. The pump sheath 902 may for example be made of a material through which IR radiation transmits such as acrylonitrile butadiene styrene (ABS), polycarbonate, nylon, polyethylene, polymethyl methacrylate (PMMA), polypropylene, polytetrafluoroethylene (PTFE), polyethylene terephthalate (PET), and polyvinyl chloride (PVC), barium fluoride, cadmium telluride, calcium fluoride, cesium bromide, cesium iodide, chalcogenide glass, fused silica, gallium arsenide, germanium, lithium fluoride, magnesium fluoride, N-BK7, potassium bromide, potassium chloride, sapphire, silicon, sodium chloride, thallium bromoiodide, zinc selenide, zinc sulfide, or combinations thereof. The pump sheath 902 may protect the drip sensor 903, the IR reflector 904, or the combination thereof from being splashed by the sanitizer 204, for example when the device 10i is actuated while the door 100 is in motion. Alternatively or in combination, the pump sheath 902 may protect other components of the device 10i including one or more of the wiring, the control circuit 208, the battery, or combinations thereof. The present disclosure thus describes a sheath 902 within the dispenser 10i, or any of the dispensers disclosed herein, that may protect the internal components of the device 10i from being splashed by the sanitizer agent 204 as it is dispensed by the dispenser 10i.

Figure 10:
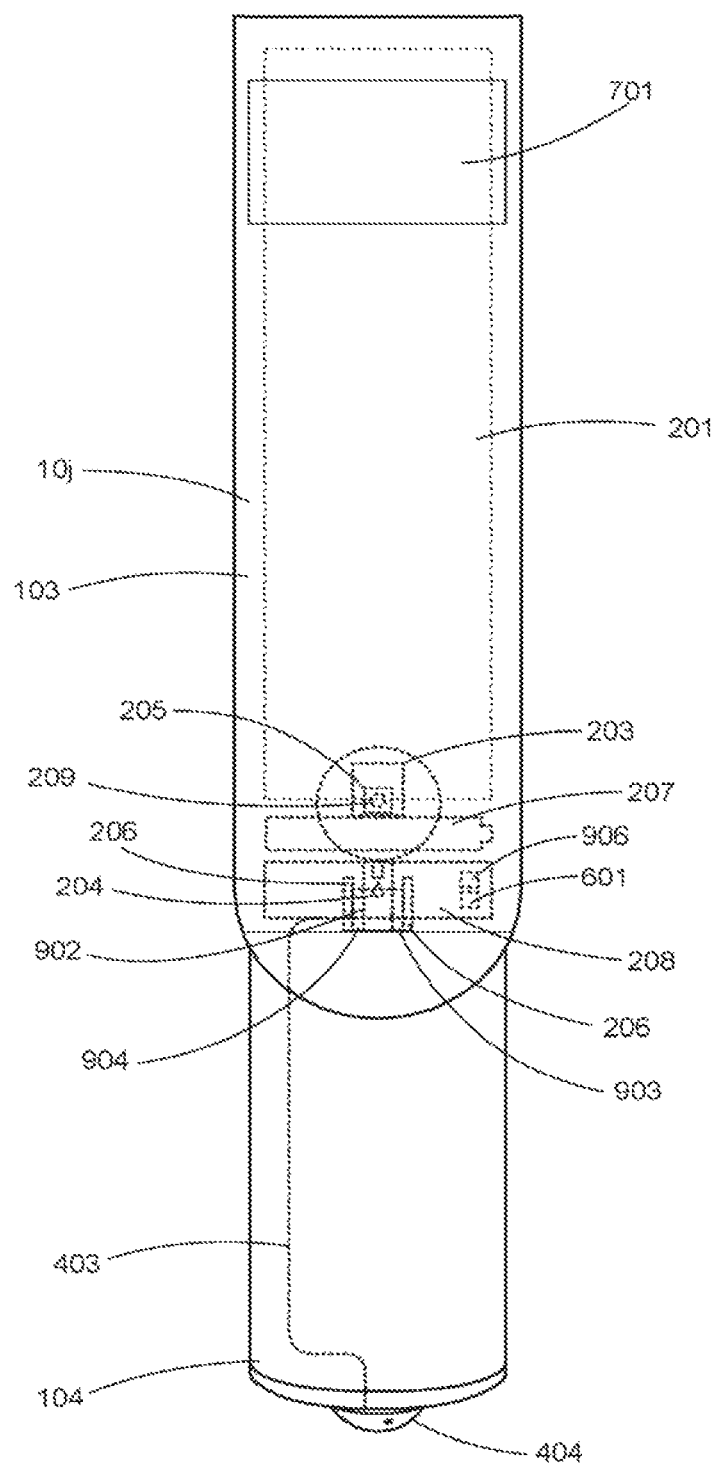
FIG. 10 depicts a front elevation view of another device to promote hand sanitization comprising a pump sheath, in accordance with embodiments.

FIG. 10 depicts a front elevation view of another device to promote hand sanitization. The dispenser 10j may be mounted on to a door comprising a handle (not shown) as described herein. The device 10j may comprise a cartridge 201 containing sanitizer agent 204 as described herein. The cartridge 201 may comprise an actuatable pump 203 in fluid communication with the cartridge 201 as described herein. The pump 203 may be positioned within the housing of the dispenser 10j between the sanitizer cartridge 201 and the actuating mechanism 103. A second hand (not shown) of the user may be used to operate the dispenser device 10j by operating the actuation mechanism 103 to dispense a sanitizer agent 204 as described herein. The device 10j may comprise a drip tray 104 positioned above the handle and used to capture sanitizer agent which does not reach the hand as described herein. An internal side of the actuating mechanism 103 may comprise a wedge 205 as described herein. The wedge 205 may comprise a sensor 209 in communication with control circuit 208 which may signal when a sanitization event has occurred as described herein. Pump support 206 may be positioned around or adjacent to the pump 203 between or below the cartridge 201 and the actuating mechanism 103 in order to provide stabilization and restrict lateral movement of the pump 203 as described herein. The device 10j may comprise a small width and a small depth as described herein. The device 10j may comprise a battery 207 and control circuit 208 to collect, collate, and/or transmit data as described herein. The control circuit 208 may comprise a transmitter 906, for example a Bluetooth transmitter, as described herein. The device 10j may be coupled to an IR detection device 404 connected to the control circuit via a wire 403 as described herein. The IR detection device 404 may detect the presence of a hand the handle and record a door opening event as described herein. The control circuit 208 may be coupled to an accelerometer 601 which may activate the IR detection device 404 only when movement of the door is detected so as to reduce power consumption as described herein. The device 10j may comprise a drip sensor 903 and IR reflector 904 which may detect and record when a drip event has occurred as described herein. The drip sensor 903 and IR reflector 904 may be positioned between the pump supports 906. The device 10j may comprise a pump sheath 902 positioned between the drip sensor 903 and IR reflector 904 so as to protect them from being splashed by the sanitizer agent 204 as described herein. The device 10j may comprise a user interface system including one or more of a display 701, one or more light sources (not shown), one or more lights (not shown), or any combination thereof.

The control circuit 208 may be used to process data transmitted from one or more of the sensor 209, the IR detection device 204, the accelerometer 601, or the drip sensor 903. The control circuit 208 may for example collect, collate, compare, or transmit data, or any combination thereof. The control circuit 208 may collect data on the total number of door opening events. The control circuit 208 may collect data on the total number of sanitization events. The control circuit 208 may be used to correlate the door opening events with the sanitization events, for example by comparing time-stamps. For example, the control circuit 208 may be used to determine when a door opening event has occurred in conjunction with a sanitization event (e.g. when the user has opted to use the dispenser 10j while opening the door). Alternatively or in combination, the control circuit 208 may be used to determine when a door opening event has occurred without a corresponding sanitization event (e.g. when the user has opted out of using the dispenser 10j). Alternatively or in combination, the control circuit 208 may be used to determine when a sanitization event has occurred without a corresponding door opening event (e.g. when the user has used the dispenser 10j without opening the door). Unlike a typical wall-mounted sanitizer dispenser which can only generate data relative to time, for example the number or percentage of sanitization events in an hour, the dispenser 10j may generate much more specific and informative data about the sanitization habits of the users passing through the door. For example, the dispenser 10j may generate data relative to the number of users passing through the door to which the dispenser 10j is mounted, for example the percentage or number of sanitization events in the last 100 users. In this way, the dispenser 10j may generate data not just on the frequency of use of the dispenser 10j, but also of the frequency with which users choose to opt out of hand sanitization, a statistic which is impossible to calculate with a standard wall-mounted dispenser. The control circuit 208 may include a processor for manipulating the data and performing correlations and calculations as described herein. Such information may be used to monitor the use of the dispenser 10j under varying user interface conditions as described herein in order to optimize the encouragement protocol, for example the timing and color of lights, of the device 10j and select the protocol which provides the highest rates of sanitization (e.g. the lowest rates of opting out).

Figure 11:
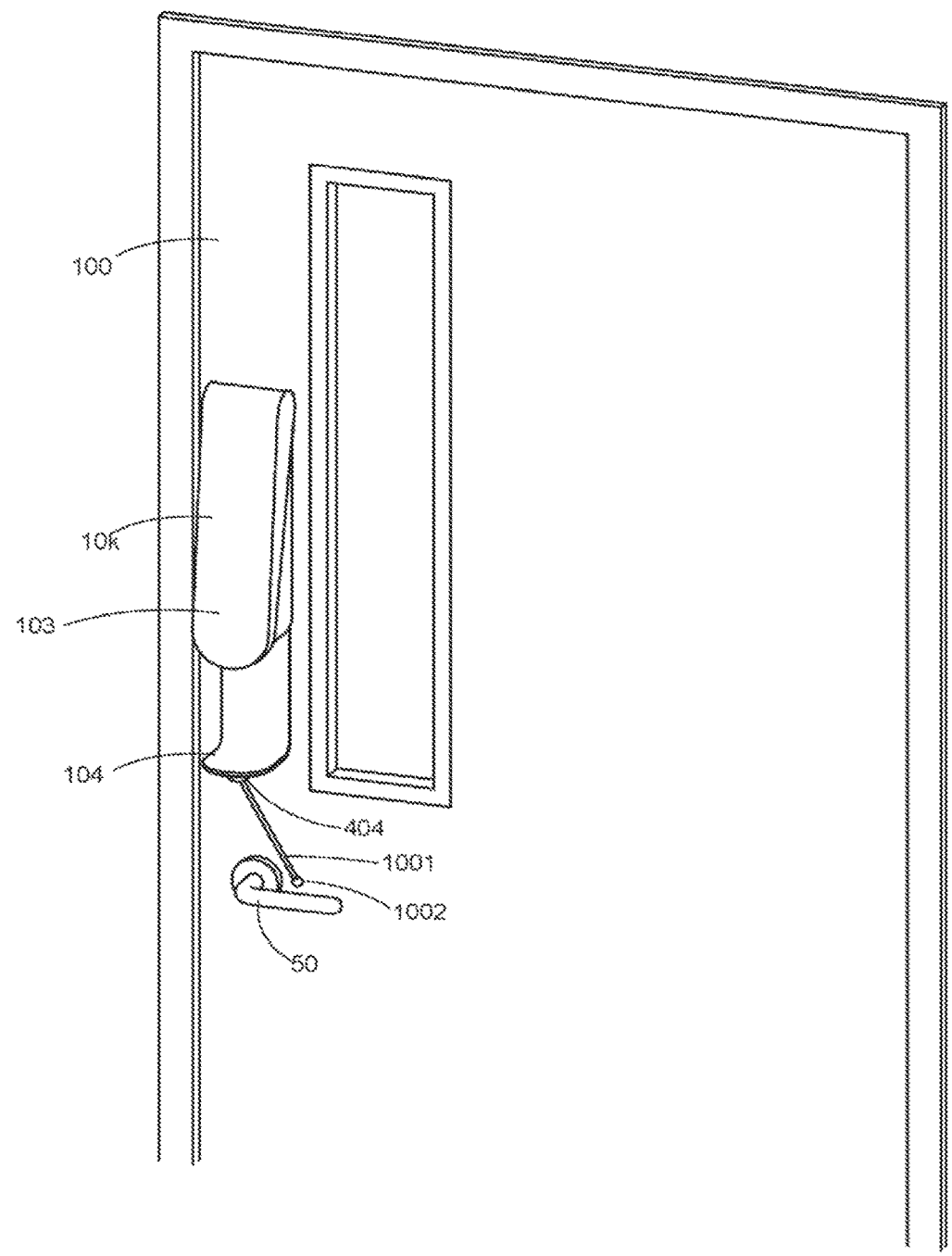
FIG. 11 depicts a perspective view of a device to promote hand sanitization comprising an installation guide, in accordance with embodiments.

FIG. 11 depicts a perspective view of a device 10k to promote hand sanitization comprising an installation guide. The device 10k may be substantially similar to any of the dispensers described herein. The dispenser 10k may be mounted on to a door 100 comprising a handle 50 as described herein. The device 10k may comprise a cartridge (not shown) containing sanitizer agent as described herein. The cartridge may comprise an actuatable pump (not shown) in fluid communication with the cartridge as described herein. A second hand (not shown) of the user may be used to operate the dispenser device 10k by operating the actuation mechanism 103 to dispense a sanitizer agent as described herein. The device 10k may comprise a drip tray 104 positioned above the handle 50 and used to capture sanitizer agent which does not reach the hand as described herein. The device 10k may comprise a small width and a small depth as described herein. The device 10k may comprise a battery (not shown) and control circuit (not shown) to collect, collate, and/or transmit data as described herein. The device 10k may be coupled to an IR detection device 404 connected to the control circuit via a wire (not shown) as described herein. The IR detection device 404 may detect the presence of a hand the handle and record a door opening event as described herein.

The device 10k may further comprise an optional installation guide 1001 in order to properly position the device 10k on the door 100 above the handle 50. The device 10k may be positioned above the handle such that it is able to reliably detect a hand when it grips the handle 50 without detecting the handle 50 itself as described herein. Thus, the placement of the device 10k may be guided by the range of the IR radiation beam emitted by IR detection device 404 so as focus the IR beam to a point above, behind, and/or in front of the handle 50 as described herein. The installation guide 1001 may for example comprise a range peg. The range peg 1001 may be inserted into the IR detection device 404 as shown and configured to mimic in physical form the range and direction of the IR beam. The range peg 1001 may further provide a ball 1002 at the distal end which corresponds to the terminal focal point of the IR beam. The ball 1002 may further aid in positioning of the device 10k and the IR detection device by providing a physical reference to indicate the termination of the IR beam. The range peg 1001 may be attached to the IR detection device 404, for example at a gimbal, such that it may be moved or rotated in order to change the direction in which the IR detection device 404, and thus the IR beam, is pointing. The range peg 1001 may be used as a guide when the dispenser is being mounted on the door 100 and removed after installation. Movement or rotation of the range peg 1001 in combination with movement of the dispenser 10k on the door 100 may ensure that the IR beam emitted by the IR detection device 404 is positioned so as to detect the presence of a hand on the handle 50 without detecting the handle 50 itself. In this way, the dispenser 10k may be easily positioned on any door or wall or above any handle, thereby increasing the utility of the dispenser 10k. After proper positioning of the device 10k on the door and of the IR detection device 404, the IR detection device 404 may be tightened into positioned so that the positioning of the IR beam is fixed above, behind, or in front of the handle 50 as desired and the range peg 1001 may be removed. The present disclosure thus describes an installation guide 1001 for use with the dispenser 10k, or any of the dispensers disclosed herein, that can provide for easy installation of the dispenser 10k on any door and above any handle.

Figure 12:
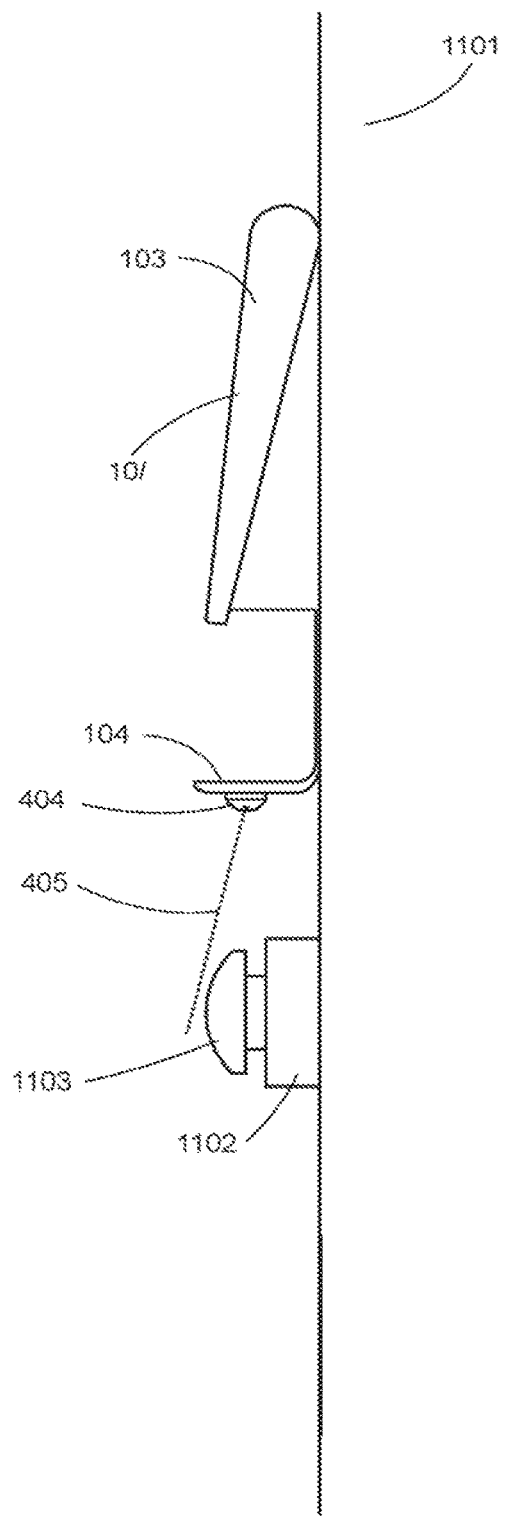
FIG. 12 depicts a side elevation view of a device to promote hand sanitization mounted on a wall above a door opening button, in accordance with embodiments.

FIG. 12 depicts a side elevation view of a device 10l to promote hand sanitization. The device 10l may be substantially similar to any of the dispensers described herein and comprise any combination of elements described herein. The dispenser 10l may be mounted to a wall 1101 in manner similar to that described with reference to mounting to a door. The device 10l may comprise a cartridge (not shown) containing sanitizer agent as described herein. The cartridge may comprise an actuatable pump (not shown) in fluid communication with the cartridge as described herein. A second hand (not shown) of the user may be used to operate the dispenser device 10l by operating the actuation mechanism 103 to dispense a sanitizer agent as described herein. The device 10l may comprise a drip tray 104 positioned so as to capture sanitizer agent which does not reach the hand as described herein. The device 10l may comprise a small width and a small depth as described herein. The device 10l may comprise a battery (not shown) and control circuit (not shown) to collect, collate, and/or transmit data as described herein. The device 10l may be coupled to an IR detection device 404 connected to the control circuit via a wire (not shown) as described herein. The wall 1101 may for example comprise a wall switch 1102 which mechanically operates a nearby door. Many automatic or handicap accessible doors feature such a wall switch 1102 on a nearby wall 1101 as it aids in easy opening of the door. The dispenser 10l may be positioned above the wall switch 1102 such that the IR radiation beam 405 terminates a point in front of the button 1103 of the wall switch 1102. Operation of the button 1103 by the hand of the user may break the IR beam 405 emitted by the IR detection device 404 which may signal a door opening event to the control circuit as described herein.

Figure 13:
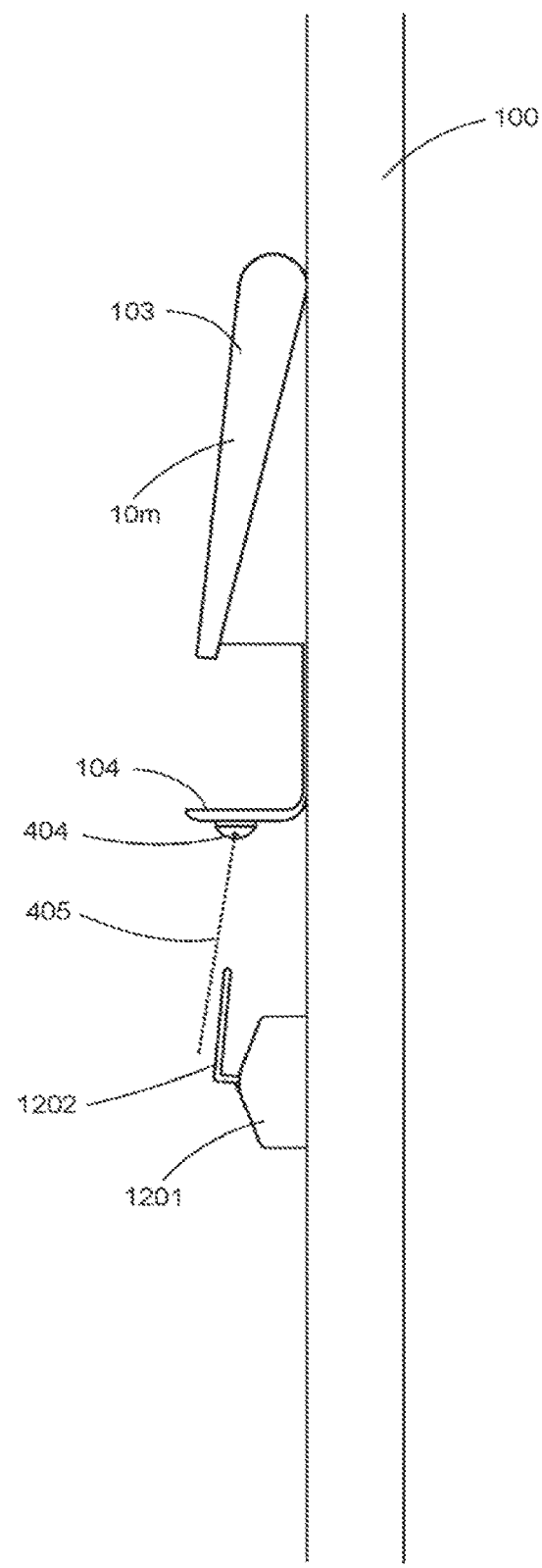
FIG. 13 depicts a side elevation view of another device to promote hand sanitization mounted on a door, in accordance with embodiments.

FIG. 13 depicts a side elevation view of another device 10m to promote hand sanitization. The device 10m may be substantially similar to any of the dispensers described herein and comprise any combination of elements described herein. The dispenser 10*m* may be mounted on to a door 100 as described herein. The device 10*m* may comprise a cartridge (not shown) containing sanitizer agent as described herein. The cartridge may comprise an actuatable pump (not shown) in fluid communication with the cartridge as described herein. A second hand (not shown) of the user may be used to operate the dispenser device 10*m* by operating the actuation mechanism 103 to dispense a sanitizer agent as described herein. The device 10*m* may comprise a drip tray 104 positioned so as to capture sanitizer agent which does not reach the hand as described herein. The device 10*m* may comprise a small width and a small depth as described herein. The device 10*m* may comprise a battery (not shown) and control circuit (not shown) to collect, collate, and/or transmit data as described herein. The device 10*m* may be coupled to an IR detection device 404 connected to the control circuit via a wire (not shown) as described herein. The IR detection device 404 may detect the presence of a hand on the handle using an IR beam 405 and record a door opening event as described herein. The door 100 may for example comprise a latched healthcare handle 1201. Many hospital doors feature such a handle as it aids in easy opening of the latched door 100. The dispenser 10*m* may be positioned above the handle 1201 such that the IR radiation beam 405 terminates a point in front of the lever 1202 of the handle 1202. Operation of the lever 1202 by the hand of the user may break the IR beam 405 which may signal a door opening event to the control circuit as described herein.

FIGS. 14A-14E depict a device 10*n* to promote hand sanitization mounted on a door configured to wrap around the door handle 50. The device 10*n* may be substantially similar to any of the dispensers described herein and comprise any combination of elements described herein. The dispenser 10*n* may be mounted on to a door 100 comprising a handle 50 as described herein. The device 10*n* may comprise a cartridge 201 containing sanitizer agent as described herein. The cartridge 201 may comprise an actuatable pump 203 in fluid communication with the cartridge as described herein. The pump 203 may be positioned within the housing of the dispenser 10*n* between the sanitizer cartridge 201 and the actuating mechanism 103. A second hand (not shown) of the user may be used to operate the dispenser device 10*n* by operating the actuation mechanism 103 to dispense a sanitizer agent as described herein. The device 10*n* may comprise a drip tray (see 104 of device 10*a*) positioned below the actuating mechanism 103 and used to capture sanitizer agent which does not reach the hand as described herein. The dispenser 10*n* may comprise a pump sheath (see 902 of device 10*i*) and/or pump supports (see 206 of device 10*b*) as described herein. The device 10*n* may comprise any combination of sensors (not shown), switches (not shown), and/or detectors (not shown) as described herein. The device 10*n* may comprise a small width and a small depth as described herein. The device 10*n* may comprise a battery (see 207 of device 10*b*) and control circuit (see 208 of device 10*b*) to collect, collate, and/or transmit data as described herein. The device 10*n* may be coupled to an IR detection device (see 404 of device 10*d*) connected to the control circuit as described herein. The IR detection device may detect the presence of a hand the handle and record a door opening event as described herein. The control circuit may be coupled to an accelerometer (see 601 of device 10*f*) which may activate the IR detection device only when movement of the door is detected so as to reduce power consumption as described herein. Alternatively or in combination the accelerometer may activate a user interface system when movement of the door is detected so as to encourage the user to use the dispenser 10*n* when passing through the door 100. The device 10*n* may comprise a user interface system including one or more of a display (see 701 of device 10*g*), one or more light sources (see 703 of device 10*g*), one or more lights, or any combination thereof.

Figure 14A:
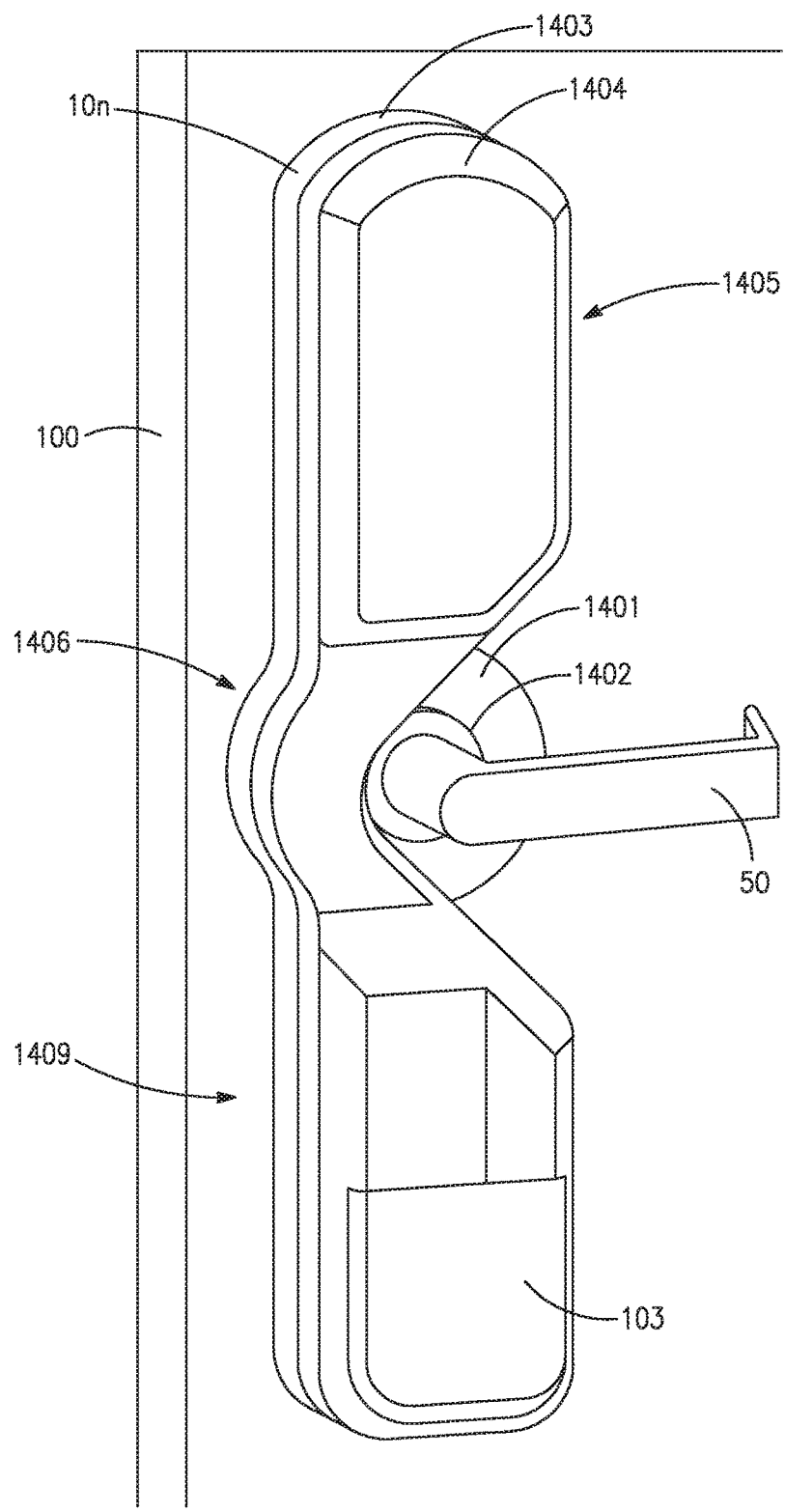
FIG. 14A depicts a perspective view of a device to promote hand sanitization mounted on a door configured to wrap around the door handle, in accordance with embodiments.
Figure 14B:
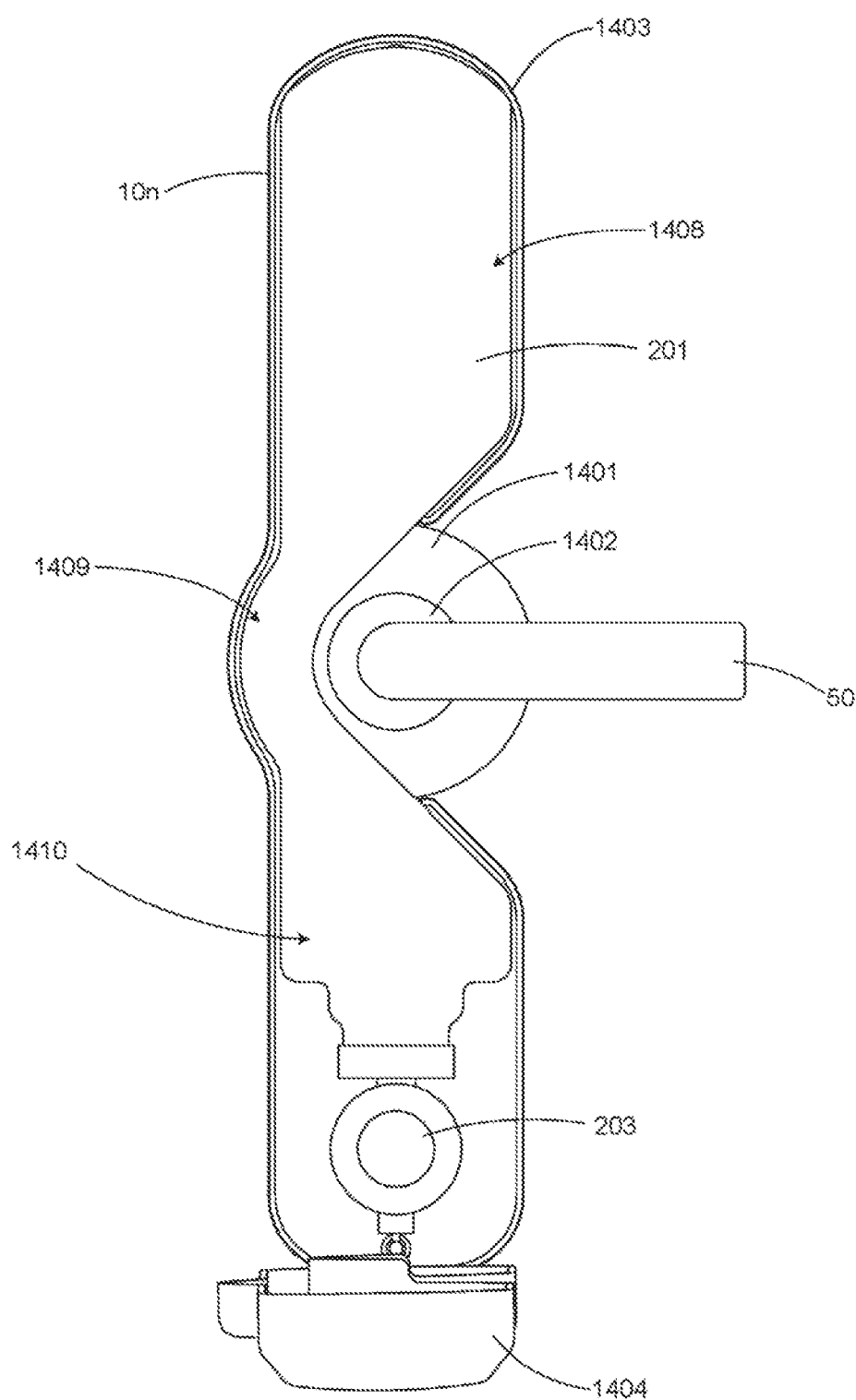
FIG. 14B depicts a front elevation view of the device of FIG. 14A with front housing open, in accordance with embodiments.
Figure 14C:
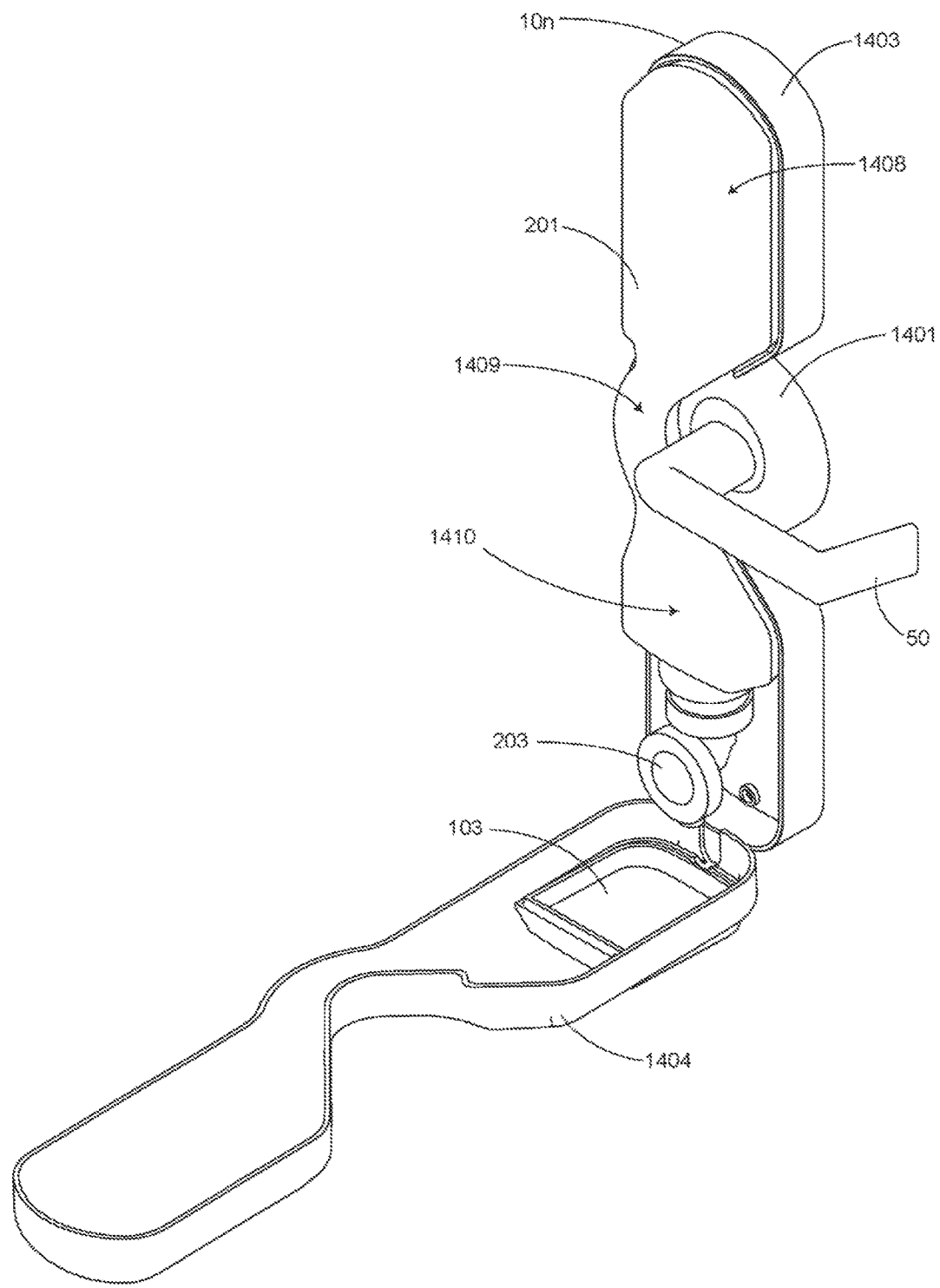
FIG. 14C depicts a perspective view of the device of FIG. 14A with front housing open, in accordance with embodiments.
Figure 14D:
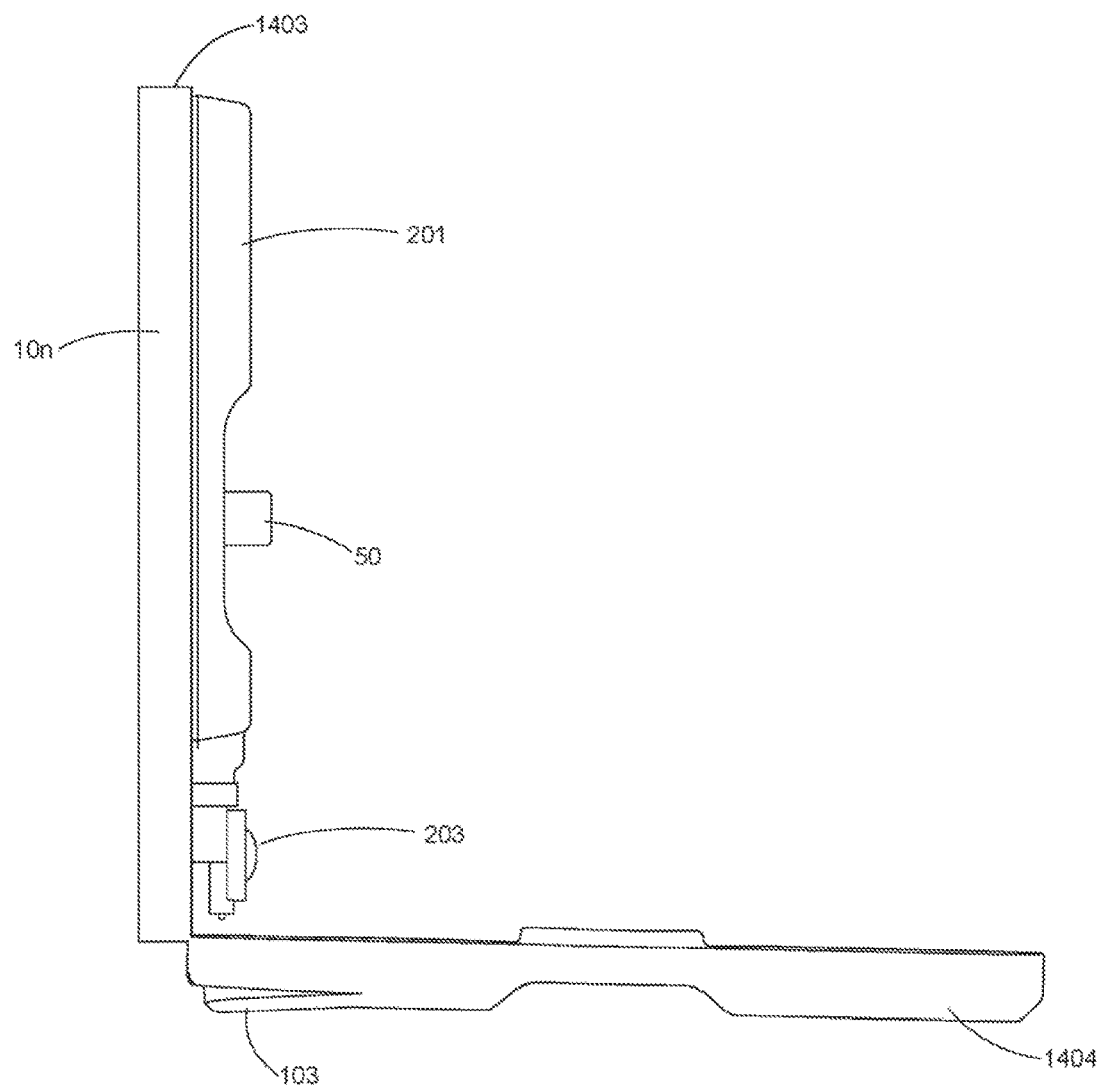
FIG. 14D depicts a side elevation view of the device of FIG. 14A with front housing open, in accordance with embodiments.
Figure 14E:
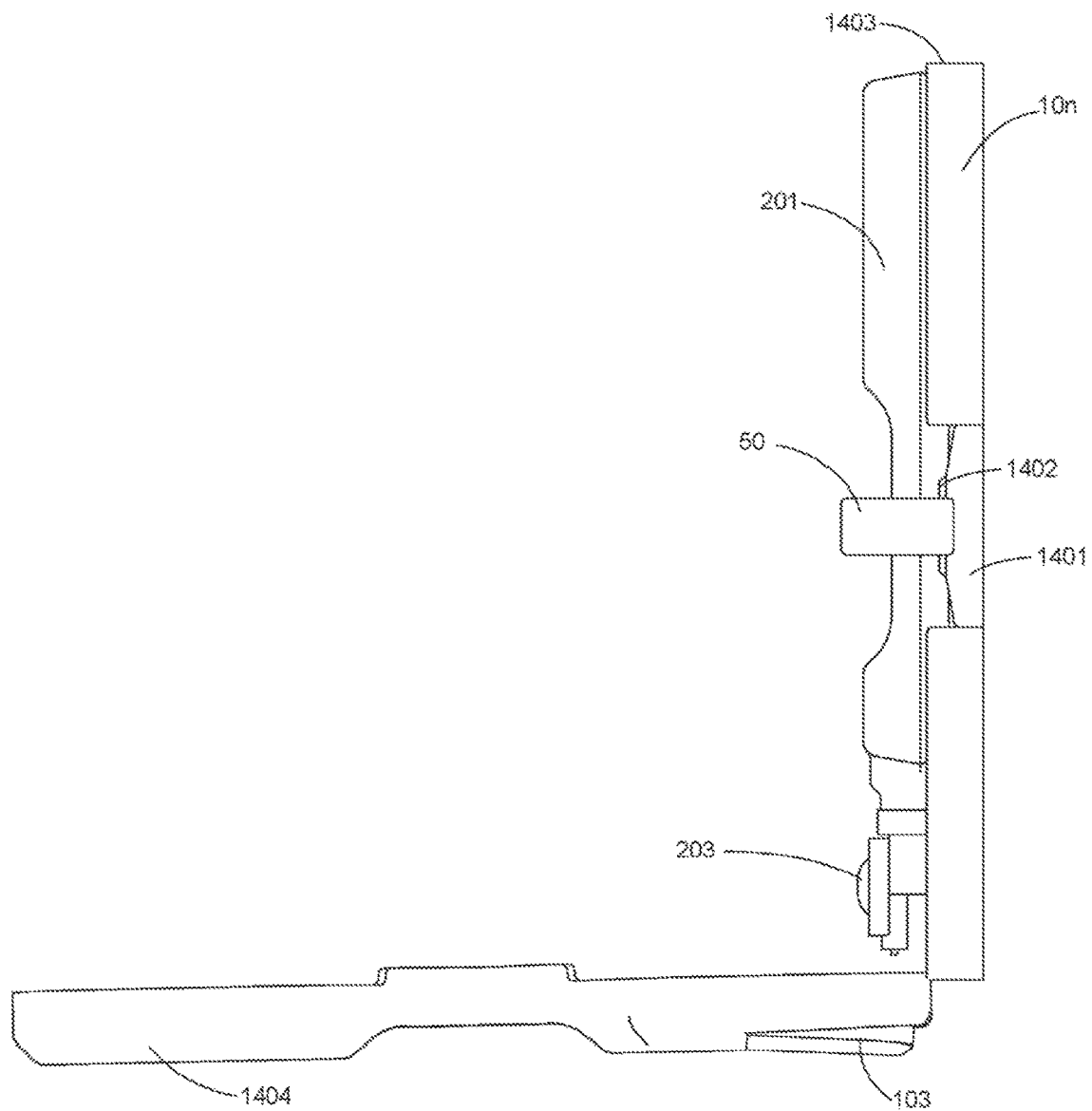
FIG. 14E depicts a side elevation view of the device of FIG. 14A with front housing open, in accordance with embodiments.

FIG. 14A depicts a perspective view of the device 10*n* configured to wrap around a rose or cover plate 1401 of a handle 50 and dispense sanitizer fluid to a user's second hand (not shown) below the handle 50 when the user's first hand (not shown) operates the handle 50. FIGS. 14B-14E depict various views of device 10*n* with front housing 1404 open. The dispenser 10*n* may be configured such that sanitizer dispensation is independent of handle 50 operation and door 100 opening. The second hand may be used to push or pull on an actuating mechanism 103. The actuation mechanism 103 may for example comprise a button located below the handle 50 when the dispenser 10*n* is mounted on the door 100. The actuation mechanism 103 may be sized and shaped such that it protrudes outwards from the door 100 in order to allow sufficient space below and/or behind the button 103 for the hand to operate the mechanism 103 without pinching the fingers of the user. The second hand may be positioned with the palm up under the actuation mechanism 103 (and, for example, above an optional drip tray). The heel of the hand 102 may press on the actuation mechanism 103 to activate the dispenser 10*n* and provide a sanitizer agent into the waiting palm of the second hand. The actuation mechanism 103 may for example comprise a button coupled by a hinge, pivot, spring, or other connection element (not shown) to a housing body which contains the sanitizer dispensing mechanism. The actuation mechanism 103 may be biased, for example by a mechanical spring, to return to its initial position when the user's hand releases the lower end of the actuation mechanism 103. Alternatively or in combination, the actuation mechanism 103 may automatically dispense the sanitizer agent into the palm of the second hand without contact between the hand and the actuation mechanism 103 as described herein.

The dispenser 10*n* may be positioned such that the hand is able to operate the dispenser 10*n* without undue effort (e.g. crossing arms/hands, reaching too high, reaching too low, etc.) in operating either the handle 50 or the device 10*n* for a majority of users. The user may be able to operate the dispenser 10*n* before, during, or after actuation of the handle 50 and opening of the door 100. In at least some instances, it may be beneficial to provide a dispenser 10*n* with an actuation mechanism 103 located below the handle 50. For example, an actuation mechanism 103 located below the handle 50 may be more ergonomic and comfortable for the user, for example by prevent crossing of the user's arms during use. Positioning the actuation mechanism 103 below the handle 50 may also make it easier to install a drip tray below the actuation mechanism 103 as the drip tray may be less likely to interfere with placement of the hand than in some instances where the drip tray is located above the handle 50.

The housing of the dispenser 10*n* may be sized and shaped to at least partially "wrap around" the rose 1401 of the handle 50. The dispenser 10*n* may thus be configured for integration with common door handles such as a lever handle 50. The dispenser 10*n* may be configured to nest around the rose 1401 and dispense sanitizer agent to the user's hand below the handle 50. The housing of the dispenser 10*n* may for example comprise an upper housing portion 1405, a lower housing portion 1407, and a narrow housing portion 1406 extending therebetween. The upper housing portion 1405 and the lower housing portion 1407 may be wider than the narrow housing portion 1406. The wider upper housing portion 1405 may taper down towards the narrow housing portion 1406 adjacent or over a portion of the rose 1401 before widening towards the lower housing portion 1407 in order to wrap the housing around the rose 1401. The narrow housing portion 1406 may for example be c-shaped so as to conform to the shape of, and fit around and/or above, the rose 1401 of the handle 50. The narrow housing portion 1406 may for example comprise a concave inner region configured to conform to the shape of the rose 1401 and optionally a convex outer surface. The narrow housing portion 1406 The dispenser 10n may be configured to be mounted on the door 100 such that the upper housing portion 1405 lies above the rose 1401 of the handle 50, the lower housing portion 1407 lies below the rose 1401, and the narrow housing portion 1406 lies adjacent the rose 1407. The housing may be sized and shaped to avoid pinching the user's hand between the handle 50 and the device 10n. Alternatively or in combination, the housing may be sized and shaped so as to provide a clean line of sight from the user to the handle.

In some instances, the housing of the dispenser 10n may be sized and shaped to fully wrap around the rose 1401 of the handle 50. The housing of the dispenser 10n may for example comprise an upper housing portion 1405, a lower housing portion 1407, and a central housing portion (not shown) therebetween. The central housing portion may for example comprise the narrow housing portion 1406 between the edge of the door and the handle 50 and an internal housing portion (not shown) around the rose 1401 below the handle 50 on the side of the rose 1401 further away from the edge of the door. The central housing portion may for example comprise a "hole" in the housing portion which can be fit adjacent or over the rose 1401 and around the handle 50. The cartridge 201 may be shaped substantially similar such that a central cartridge portion (not shown) comprises a "hole" around which sanitizer agent can flow towards the actuatable pump 203.

A typical door handle 50 comprising a rose 1401 may comprise a shoulder 1402 which couples the portion of the handle 50 which the hand grips to the rose 1401. A typical rose 1401 may comprise a maximum outer dimension of about 3.6 inches, for example no more than about 3.57 inches. A typical shoulder 1402 may comprise a maximum height above the door 100 of about 0.7 inches, for example no more than about 0.66 inches. The housing may be sized and shaped so as to nest above and/or adjacent the rose 1401 and/or the shoulder 1402 of the handle 50 when mounted on the door 100. The housing may be sized and shaped such that an edge of the dispenser 10n is positioned no more than about 0.6 inches from the edge of the rose 1401 in order to ensure that the dispenser 10n does not hit the door frame or door jamb when the door is opened or closed by the user.

In some instances, the dispenser 10n may further comprise a rose-like plate which may be configured to replace the original rose 1401 of the handle 50 upon installation. The rose-like plate may be attachable to the device 10n or may be an integral part of the device 10n. A typical door handle 50 comprising a rose 1401 may be separable from the rose into two distinct elements—the rose 1401 and the handpiece. To install a dispenser 10n comprising a rose-like plate, the handpiece and the rose 1401 may be removed from the door and separated from one another. The rose-like plate of the dispenser may be installed on the door approximately where the original rose was (or, alternatively, a new location may be chosen) and the handpiece may be "locked in" by re-attachment of the handpiece to the door and to the rose-like plate. Alternatively, the rose-like plate may be configured to fit over the rose 1401 (for example by sliding the handpiece through the rose-like plate, opening the rose-like plate—for example at a hinge—and latching the plate to the handpiece, or by any other mechanism known to one of ordinary skill in the art) such that installation may occur without removing the original rose 1401.

The housing of the dispenser 10n may comprise a back housing portion 1403 and a front housing portion 1404. The housing may contain a cartridge 201 containing sanitizer agent. The cartridge 201 may be positioned within the dispenser 10n between a back housing portion 1403 and a front housing portion 1404. The cartridge 201 may be one or more of removable, replaceable, or refillable. The cartridge 201 may comprise a volume of sanitizer agent or fluid 204 comparable to other dispensers known in the art, for example within a range of about 500 ml to about 1000 ml, about 600 ml to about 800 ml, or about 600 ml. The cartridge 201 may comprise an upper cartridge portion 1408, a lower cartridge portion 1410, and a narrow cartridge portion 1409 therebetween which are shaped substantially similarly to and configured to fit within the upper housing portion 1405, lower housing portion 1407, and narrow housing portion 1406, respectively. The cartridge 201 may for example be molded, for example blow-molded, and may comprise an ambidextrous design to allow for use in devices configured to wrap around a handle on the left and/or right of a door. The cartridge 201 may be made of any suitable material known to one of ordinary skill in the art, for example high-density polyethylene.

The cartridge 201 may be accessed for example by pulling on the upper end of the front housing portion 1404 so as to cause rotation of the front housing portion 1404 about a pivot (not shown) coupling the lower end of the front housing portion 1404 and the lower end of the back housing portion 1403. The front housing portion 1404 may move towards the user and downwards to expose the cartridge 201, for example to allow for replacement of an empty cartridge 201. Alternatively or in combination, the front housing portion 1404 may be detachable from the back housing portion 1403 and removable to provide access to the cartridge 201. Alternatively or in combination, the device 10n may comprise an access door on the actuation mechanism 103, front housing portion 1404, or back housing portion 1403 which may provide access to the cartridge 201 for replacement or maintenance.

The cartridge 201 may comprise an actuatable pump 203 in fluid communication with the cartridge 201. The actuatable pump 203 may for example be a collapsible pump, a compressible pump, a foaming pump, a spray pump, or the like. The pump 203 may for example comprise a vented disc pump system as shown. The pump 203 may be substantially similar to any of the pumps described herein. The pump 203 may be positioned within the housing of the dispenser 10n between the sanitizer cartridge 201 and the actuating mechanism 103. An internal side of the actuating mechanism 103 may be brought into contact with the pump 203 by pressing on the button 103 in order to compress the pump 203 and dispense sanitizer agent into the hand. The pump 203 may be refilled with sanitizer agent when the compression is released as the actuation mechanism 103 is biased back to its initial position after the user's hand is removed from the actuation mechanism 103.

The device 10n may further comprise an optional user interface system configured to interact with the user as described herein. For example, the user interface system may comprise one or more colored lights which are activated by an optional accelerometer or proximity sensor operably coupled to the device 10*n* as described herein. The colored lights may for example be located behind the actuation mechanism 103 such that, when the actuation mechanism 103 comprises a light-transmissive material and the lights are lit, the colored lights shine through the actuation mechanism 103 in order to direct the gaze of the user towards the actuation mechanism 103 and cue sanitization behavior. An accelerometer may detect movement of the door 100, for example movement caused by the user's hand contacting the handle 50, and activate the colored lights to display a red or blue light to the user. After actuating the button 103, the colored lights may turn green to reward the user for sanitizing their hands.

The device 10*n* may further comprise an optional electronic system to monitor the presence of a hand on the handle 50. A door sensor (not shown) may be coupled to the housing, for example to the upper housing portion 1405, the narrow hosing portion 1406, or the lower housing portion 1407, for example attached or integral to the narrow housing portion 1406 and/or the tapering between the narrow housing portion 1406 and the lower and/or upper housing portions 1405, 1407. The door sensor may for example be an ultrasonic sensor or an IR detection device as described herein. The IR detection device may be configured to emit a narrow beam or field of IR radiation a set distance downward (e.g. when the door sensor is located above the handle 50), upward (e.g. when the door sensor is located below the handle 50), or relatively parallel to the ground (e.g. when the door sensor is located or configured to point to a point in front of or behind the handle 50). The IR detection device may be configured to emit the beam towards a pre-determined point above, below, behind, or in front of the handle 50. When the hand grips the handle 50, and/or when the hand actuates the handle 50 downwards (or upwards), the hand may break the IR beam and cause IR radiation to be reflected back towards the IR detection device as described herein.

The dispenser 10*n* may be easily mounted on the door 100 so as to wrap around the rose 1401. The dispenser 10*n* may be mounted so as to be disposed over the rose 1401. The front housing portion 1404 may be opened and the cartridge 201 (if installed within the housing previously) may be removed so as to expose the inner side of the back housing portion 1403. The housing may be positioned about the rose 1401 such that the upper housing portion 1405 is positioned above the rose 1401, the lower housing portion 1407 is positioned below the rose 1401, and the narrow housing portion 1406 is positioned adjacent the rose 1401. The housing may be leveled to be approximately parallel to edges of the door 100. The back housing portion 1403 may be fastened to the door 100, for example using screws or other fasteners known to one of ordinary skill in the art or described herein such as double-sided adhesive. The cartridge 201 comprising the vented disc pump 203 may be installed within the back housing portion 1403. The front housing portion 1404 may then be closed and secured (e.g. by a press fit, latch, or other locking mechanism) to complete the installation of the device 10*n*.

Figure 15A:
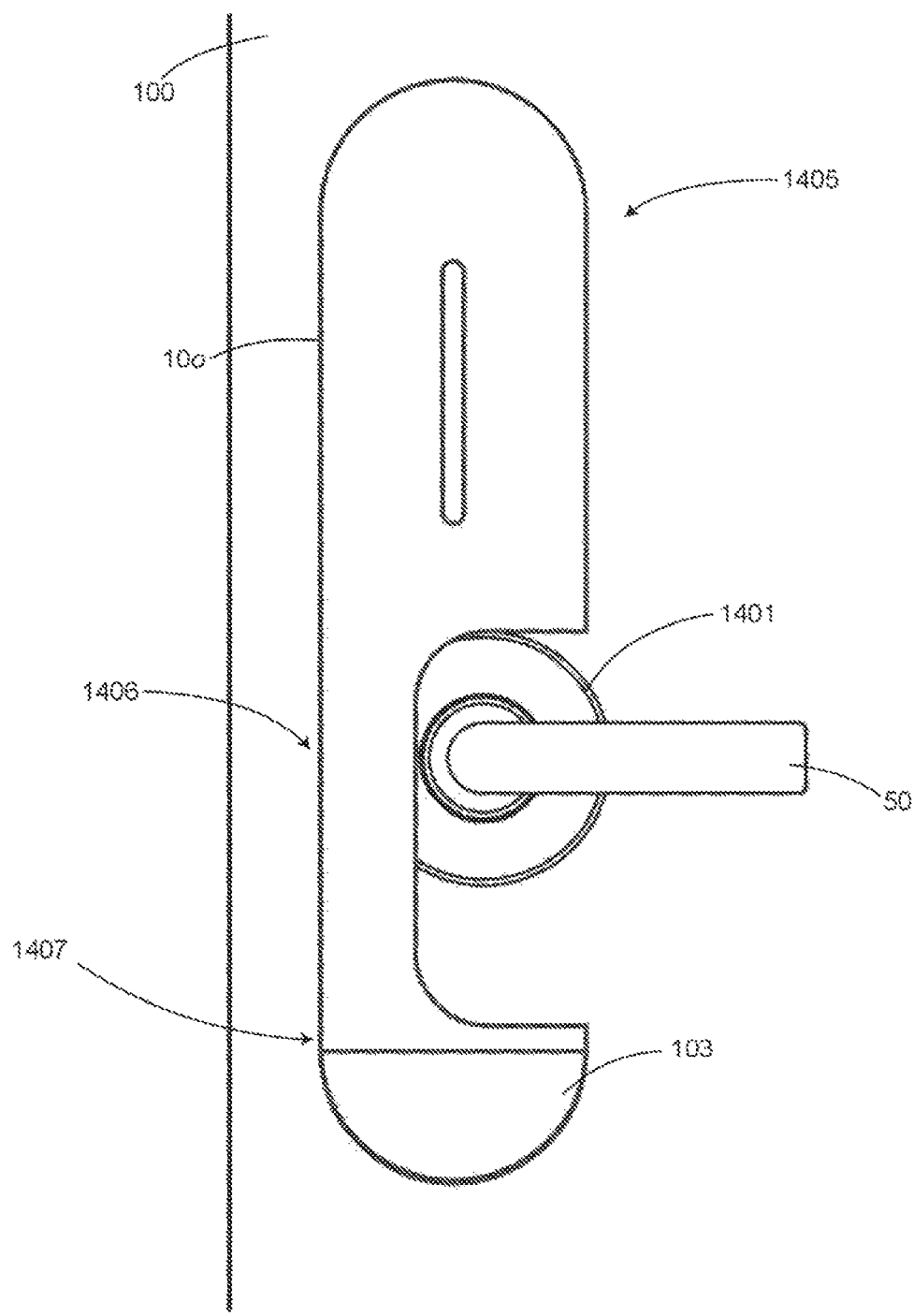
FIG. 15A depicts a front elevation view of another device to promote hand sanitization mounted on a door configured to wrap around the door handle, in accordance with embodiments.
Figures 15B, 15C:
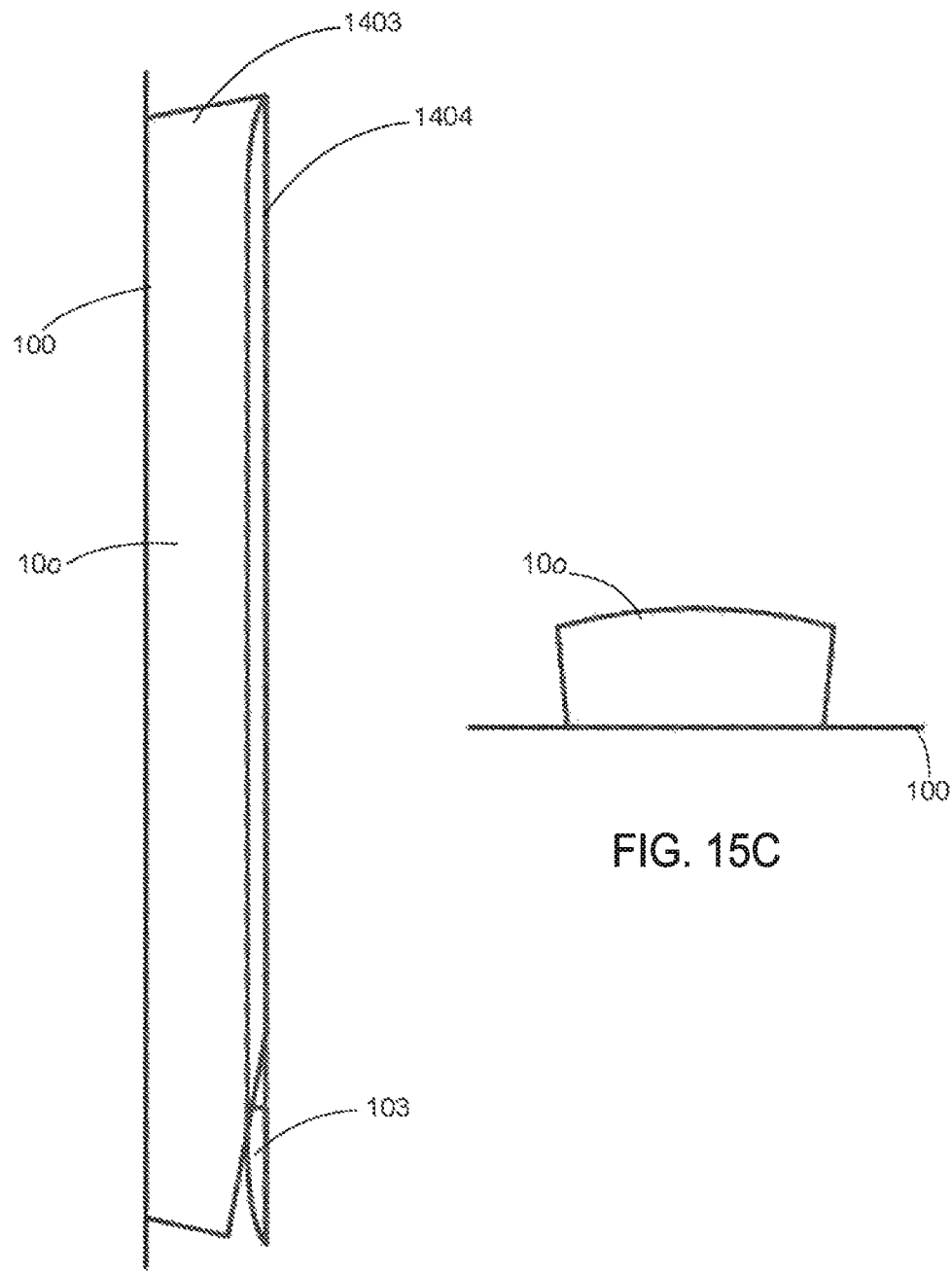
FIG. 15B depicts a side elevation view of the device of FIG. 15A, in accordance with embodiments.
FIG. 15C depicts a plan view of the device of FIG. 15A, in accordance with embodiments.

FIGS. 15A-15C depict a device 10*o* to promote hand sanitization mounted on a door configured to wrap around the door handle. The device 10*o* may be substantially similar to any of the dispensers described herein and comprise any combination of elements described herein. FIG. 15A depicts a front elevation view of the dispenser 10*o*. The dispenser 10*o* may be mounted on to a door 100 comprising a handle 50 as described herein. The housing of the dispenser 10*o* may comprise a back housing portion 1403 and a front housing portion 1404 as described herein. The housing may comprise a wide upper portion 1405, a narrow portion 1406, and a wide lower portion 1407 and may have a slotted region that is shaped to receive a portion of the door handle so as to wrap around the rose 1401 of the handle 50 as described herein. The device 10*o* may comprise a cartridge (not shown) containing sanitizer agent as described herein. The cartridge may be positioned within the dispenser 10*o* between a back housing portion 1403 and a front housing portion 1404 as described herein. The cartridge may be shaped so as to correspond to the shape of the housing of the dispenser 10*o* as described herein. The cartridge may comprise an actuatable pump (not shown) in fluid communication with the cartridge as described herein. The pump may be positioned within the housing 1403, 1404 of the dispenser 10*o* between the sanitizer cartridge and the actuating mechanism 103. A second hand (not shown) of the user may be used to operate the dispenser device 10*o* by operating the actuation mechanism 103 to dispense a sanitizer agent as described herein. The device 10*o* may comprise a drip tray (not shown) positioned below the actuating mechanism 103 and used to capture sanitizer agent which does not reach the hand as described herein. The dispenser 10*o* may comprise a pump sheath (not shown) and/or pump supports (not shown) as described herein. The device 10*o* may comprise any combination of sensors (not shown), switches (not shown), and/or detectors (not shown) as described herein. The device 10*o* may comprise a small width and a small depth as described herein. FIG. 15B depicts a side elevation view of the device 10*o* mounted on door 100 around a handle (not shown). The dispenser 10*o* may have a depth much smaller than that of a standard sanitizer dispenser in order to passers-by from inadvertently striking the device 10*o* or the device from striking the wall when the door 100 is fully opened as described herein. FIG. 15C depicts a plan view of the device 10*o* mounted on door 100. The device 10*o* may comprise a small enough width and depth such that opening of the door does not result in the dispenser 10*o* striking the door frame as described herein. The device 10*o* may comprise a battery (not shown) and control circuit (not shown) to collect, collate, and/or transmit data as described herein. The device 10*o* may be coupled to an IR detection device (not shown) connected to the control circuit as described herein. The IR detection device may detect the presence of a hand the handle and record a door opening event as described herein. The control circuit may be coupled to an accelerometer (not shown) which may activate the IR detection device only when movement of the door is detected so as to reduce power consumption as described herein. Alternatively or in combination the accelerometer may activate a user interface system when movement of the door is detected so as to encourage the user to use the dispenser 10*o* when passing through the door 100. The device 10*o* may comprise a user interface system including one or more of a display (not shown), one or more light sources (not shown), one or more lights (not shown), or any combination thereof as described herein.

The device 10*o* may be substantially similar to the device 10*n* except that the narrow housing portion 1406, and corresponding narrow cartridge portion (not shown), may be longer so as to provide additional space around the handle 50 in which the hand may operate the handle 50. This additional space may facilitate movement of the handle 50 without pinching the user's hand between the handle 50 and the device 10*o*. Alternatively or in combination, the space may promote visualization of the handle by the user by providing a clean line of sight. The device 10o may generally have the same size and shape, for example the same external dimensions, as the device 10n, or any of the devices described herein. The lower housing portion 1407, and corresponding lower cartridge portion (not shown), may be shortened in order to accommodate the extra length of the narrow housing portion 1406. The lower cartridge portion may comprise the actuatable pump (not shown) and the actuation mechanism 103. The device 10o may further comprise a window located in the upper housing portion 1405 which may show a user the level of the sanitizer agent within the cartridge 201 without needing to open the housing.

One of skill in the art will recognize that the elements of the dispenser embodiments described herein may be combined in many ways. The dispenser may comprise any combination of actuating mechanisms, pump sheaths, pump supports, actuatable pumps, or other dispenser elements as described herein. The dispenser may be placed on any door, wall, or other surface of interest as described herein. The dispenser may be positioned above or around any handle, wall switch, or other known door actuating mechanism as described herein. The dispenser may comprise any combination of sensors, switches, or detectors described herein or known in the art. The dispenser may be configured with any combination of displays, lights, sounds, or other user interface options as described herein or known in the art. The dispenser may comprise any combination of circuitry or data processing elements as described herein or known in the art.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A hand sanitization device comprising:
a housing configured to be mounted on a door comprising a handle, wherein the housing comprises an upper housing portion, a lower housing portion, and a narrow housing portion therebetween, wherein the handle comprises a rose, and wherein the housing is configured to be mounted on the door such that the upper housing portion lies above the rose, the lower housing portion lies below the rose, and the narrow housing portion lies adjacent the rose and conforms thereto;
a cartridge disposed within the housing, wherein the cartridge contains a sanitizer agent;
an actuatable pump disposed in the housing and operably coupled with the cartridge, wherein actuation of the actuatable pump causes the cartridge to dispense the sanitizer agent to a user's hand;
an actuation mechanism operably coupled to the actuatable pump and movable from a first position to a second position, wherein movement of the actuation mechanism from the first position to the second position by the user's hand actuates the pump; and
a pump sheath adjacent the pump and coupled to the cartridge, the pump sheath acting to protect internal components in the housing from being splashed by the sanitizer agent when dispensed from the pump.

2. The hand sanitization device of claim 1, further comprising a user interface system the user interface system comprising an indicator element, wherein the user interface system is configured to encourage the user to sanitize their hands.

3. The hand sanitization device of claim 1, further comprising a proximity sensor configured to sense the user approaching the door, wherein the proximity sensor is configured to activate one or more of a user interface system or a door sensor when the approaching user is sensed.

4. The hand sanitization device of claim 1, further comprising a control circuit configured to collect data, collate data, or transmit data, wherein the data comprises a drip event, a door opening event, a sanitization event, or a ratio of sanitization events to door opening events for a predetermined number of users.

5. A hand sanitization device comprising:
a housing configured to be mounted on a door comprising a handle, wherein the handle comprises a rose, wherein the housing is configured to be mounted on the door such that an upper housing portion lies above the rose, a lower housing portion lies below the rose, and a narrow housing portion lies adjacent the rose and conforms thereto;
a cartridge disposed within the housing, wherein the cartridge contains a sanitizer agent;
an actuatable pump disposed in the housing and operably coupled with the cartridge, wherein actuation of the actuatable pump causes the cartridge to dispense the sanitizer agent to a user's hand; and
an actuation mechanism operably coupled to the actuatable pump and movable from a first position to a second position, wherein movement of the actuation mechanism from the first position to the second position actuates the pump.

6. The hand sanitization device of claim 5, wherein the cartridge comprises an upper cartridge portion, a lower cartridge portion, and a narrow cartridge portion therebetween which are shaped substantially similarly to the upper housing portion, lower housing portion, and narrow housing portion, respectively.

7. The hand sanitization device of claim 5, further comprising a user interface system the user interface system comprising an indicator element, wherein the user interface system is configured to encourage the user to sanitize their hands.

8. The hand sanitization device of claim 5, further comprising a proximity sensor configured to sense the user approaching the door, wherein the proximity sensor is configured to activate one or more of a user interface system or a door sensor when the approaching user is sensed.

9. The hand sanitization device of claim 5, further comprising a control circuit configured to collect data, collate data, or transmit data, wherein the data comprises a drip event, a door opening event, a sanitization event, or a ratio of sanitization events to door opening events for a predetermined number of users.

* * * * *